United States Patent
Osborne et al.

(10) Patent No.: US 10,182,981 B2
(45) Date of Patent: *Jan. 22, 2019

(54) METHOD OF REGULATING A SKIN CONDITION

(71) Applicant: The Procter & Gamble Company, Cincinnati, OH (US)

(72) Inventors: Rosemarie Osborne, Oxford, OH (US); Lisa Ann Mullins, West Chester, OH (US); Michael Koganov, White Plains, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/368,853

(22) Filed: Dec. 5, 2016

(65) Prior Publication Data

US 2017/0157031 A1 Jun. 8, 2017

Related U.S. Application Data

(60) Provisional application No. 62/264,604, filed on Dec. 8, 2015.

(51) Int. Cl.
| | |
|---|---|
| *A61K 8/97* | (2017.01) |
| *A61Q 19/00* | (2006.01) |
| *A61Q 5/02* | (2006.01) |
| *A61K 8/368* | (2006.01) |
| *A61K 8/36* | (2006.01) |
| *A61K 8/23* | (2006.01) |
| *A61K 8/41* | (2006.01) |
| *A61K 8/34* | (2006.01) |
| *A61Q 19/02* | (2006.01) |
| *A61Q 19/08* | (2006.01) |

(52) U.S. Cl.
CPC .................. *A61K 8/97* (2013.01); *A61K 8/23* (2013.01); *A61K 8/345* (2013.01); *A61K 8/36* (2013.01); *A61K 8/368* (2013.01); *A61K 8/41* (2013.01); *A61Q 19/008* (2013.01); *A61Q 19/02* (2013.01); *A61Q 19/08* (2013.01); *A61K 2800/30* (2013.01); *A61K 2800/524* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 5,393,526 A | 2/1995 | Castro | |
| 5,811,085 A | 9/1998 | Halloran | |
| 6,136,304 A | 10/2000 | Pyles | |
| 6,238,674 B1 * | 5/2001 | Renimel | A61K 8/97 424/401 |
| 6,238,678 B1 * | 5/2001 | Oblong | A61K 8/42 424/401 |
| 7,442,391 B2 | 10/2008 | Koganov | |
| 7,537,791 B2 | 5/2009 | Koganov | |
| 2002/0048594 A1 * | 4/2002 | Breton | A61K 8/97 424/401 |
| 2004/0037895 A1 * | 2/2004 | Zhu | A61K 31/19 424/697 |
| 2008/0206373 A1 | 8/2008 | Millikin et al. | |
| 2010/0028463 A1 * | 2/2010 | Kim | A61K 8/97 424/725 |
| 2012/0201768 A1 | 8/2012 | Swanson et al. | |
| 2013/0164323 A1 | 6/2013 | Richards et al. | |
| 2017/0157029 A1 | 6/2017 | Osborne et al. | |
| 2017/0157030 A1 | 6/2017 | Osborne et al. | |
| 2017/0157032 A1 | 6/2017 | Osborne et al. | |

FOREIGN PATENT DOCUMENTS

| | | |
|---|---|---|
| BR | 102013029865 A2 | 10/2015 |
| WO | WO2004054598 A1 | 7/2004 |
| WO | WO2014076055 A1 | 5/2014 |

OTHER PUBLICATIONS

Seek Beauty, No. 593 Serum—Age Defying Spot Treatment, http://seekbeauty.com/product/no-593-age-defying-spot-treatment/,m retrieved online on Aug. 21, 2017 (Year: 2017).*
Terrazas, Benzophenone guttiferone A from Garcinia achachairu Rusby (Clusiaceae) Presents Genotoxic Effects in Different Cells of Mice, Nov. 2013 | vol. 8 | Issue 11 | e76485 (Year: 2013).*
Wilson, Seek Beauty: An Interview with Amy Greeson, http://ifthemuumuufits.com/seek-beauty-an-interview-with-amy-greeson/, Oct. 6, 2015 (Year: 2015).*
AmyG Cosmetics (Seek Beauty)—Guys Family Pharmacy, https://www.guysfamilypharmacy.com/amyg-cosmetics-seek-beauty/, Jun. 3, 2015 (Year: 2015).*
Garcinia Humilis, T.K. Lim, Edible Medicinal and Non-Medicinal Plants: vol. 2, Fruits, 59 DOI 10.1007/978-94-007-1764-0_9, Springer Science+Business Media B.V. 2012 (Year: 2012).*
Janssens et al, Protein contact dermatitis: myth or reality?, British Journal of Dermatology 1995; 132: 1-6, (Year: 1995).*
Alves et al., Biological Screening of Brazilian Medicinal Plants, Mem Inst Oswaldo Cruz, vol. 95(3), 2000, pp. 367-373.
AmyG Cosmetics (Seek Beauty)—Guys Family Pharmacy, https://www.guysfamilypharmacy.com/amyg-cosmetics-seek-beauty/, Mar. 6, 2015.
Barbosa et al., Germinação de sementes e desenvolvimento inicial de plântulas de achachairu, Rev. Bras. Frutic., vol. 30, No. 1, pp. 263-266, 2008.

(Continued)

*Primary Examiner* — Jennifer A Berrios
(74) *Attorney, Agent, or Firm* — John G. Powell

(57) ABSTRACT

A method of regulating a skin conditions that includes applying a safe and effective amount of *achachairu* to a target portion of skin in need of treatment or where treatment is desired. The *achachairu* can be in the form of a bioactive ingredient that exhibits anti-inflammatory, anti-oxidant, and/or anti-aging properties, and which is free or substantially free of benzophenones and/or protein. The *achachairu* ingredient may be a serum fraction and/or an extract, and may be incorporated into a skin care composition formulated for topical use on skin.

10 Claims, 6 Drawing Sheets

(56) References Cited

OTHER PUBLICATIONS

Dal Molin et al., Phytochemical Analysis and Antinociceptive Properties of the Seeds of Garcinia achachairu, Archives of Pharmacal Research vol. 35, No. 4, pp. 623-631, 2012.
International Search Report and Written Opinion of the International Searching Authority, PCT/US2016/064888, dated Feb. 20, 2017, 14 pages.
Mariano et al., Composição química de Garcinia achachairu Rusby (Clusiaceae), 22o Simpósio de Plantes Medicinais, Dec. 31, 2012, http://www.ufrgs.br/spmb2012/Trabalhos/3430_1337110179_Simpósio_BG2012.
Seek Beauty, No. 593 Serum—Age Defying Spot Treatment, http://seekbeauty.com/product/no-593-age-defying-spot-treatment/, retrieved online on Aug. 21, 2017.
Terrazas, Benzophenone guttiferone A from Garcinia achachairu Rusby (Clusiaceae) Presents Genotoxic Effects in Different Cells of Mice, PLOS ONE, vol. 8, Issue 11, Nov. 2013.
Wilson, Seek Beauty: An Interview with Amy Greeson | if the Muumuu Fits, Jun. 10, 2015, http://ifthemuumuufits.com/SEEK-BEAUTY-AN-INTERVIEW-WITH-AMY-GREESON/.
Achacha.com. Internet archive date: Mar. 1, 2014. [Retrieved from the Internet on: Jul. 31, 2018]. Retrieved from: URL: https://web.archive.org/web/20140301023738/http://achacha.com.au/eatingandserving/achacha-skin-infusion/. (Year: 2014).
Anonymous: Mangosteen Review—Health Benefits Side Effects and Risks, http://www.health-report.co.uk/mangosteen.htm.
Chapter 84: Solutions, Emulsions, Suspensions, and ExtractivesNairn, JG. "Solutions, Emulsions, Suspensions, and Extractives" from Remington's Pharmaceutical Science: 17th Ed. Joseph P. Remington. Mack Publishing Co., 1985. pp. 1492. (Year: 1985).
EWG's Skin Deep, Sucrose. Internet archive date: May 30, 2011. [Retrieved online on Jul. 23, 2018]. Retrieved from the Internet on: Jul. 31, 2018. Retrieved from: URL: https://web.archive.org/web/20110530224932/https://www.ewg.org/skindeep/ingredient/706364/SUCROSE/:. (Year: 2011).
Grumman, R. "5 Foods for Healthy Skin" Internet Posting Date: Oct. 31, 2013. [Retrieved from the Internet on: Jun. 23, 2018]. Retrieved from: URL: http://www.health.com/beauty/5-foods-for-healthy-skin. (Year: 2013).
International Search Report and Written Opinion of the International Searching Authority, PCT/US2016/064886, dated Apr. 4, 2017, 14 pages.
International Search Report and Written Opinion of the International Searching Authority, PCT/US2016/064887, dated Feb. 16, 2017, 15 pages.
International Search Report and Written Opinion of the International Searching Authority, PCT/US2016/064889, dated Mar. 10, 2017, 9 pages.
All Office Actions, U.S. Appl. No. 15/368,832.
All Office Actions, U.S. Appl. No. 15/368,844.
All Office Actions, U.S. Appl. No. 15/368,930.

* cited by examiner

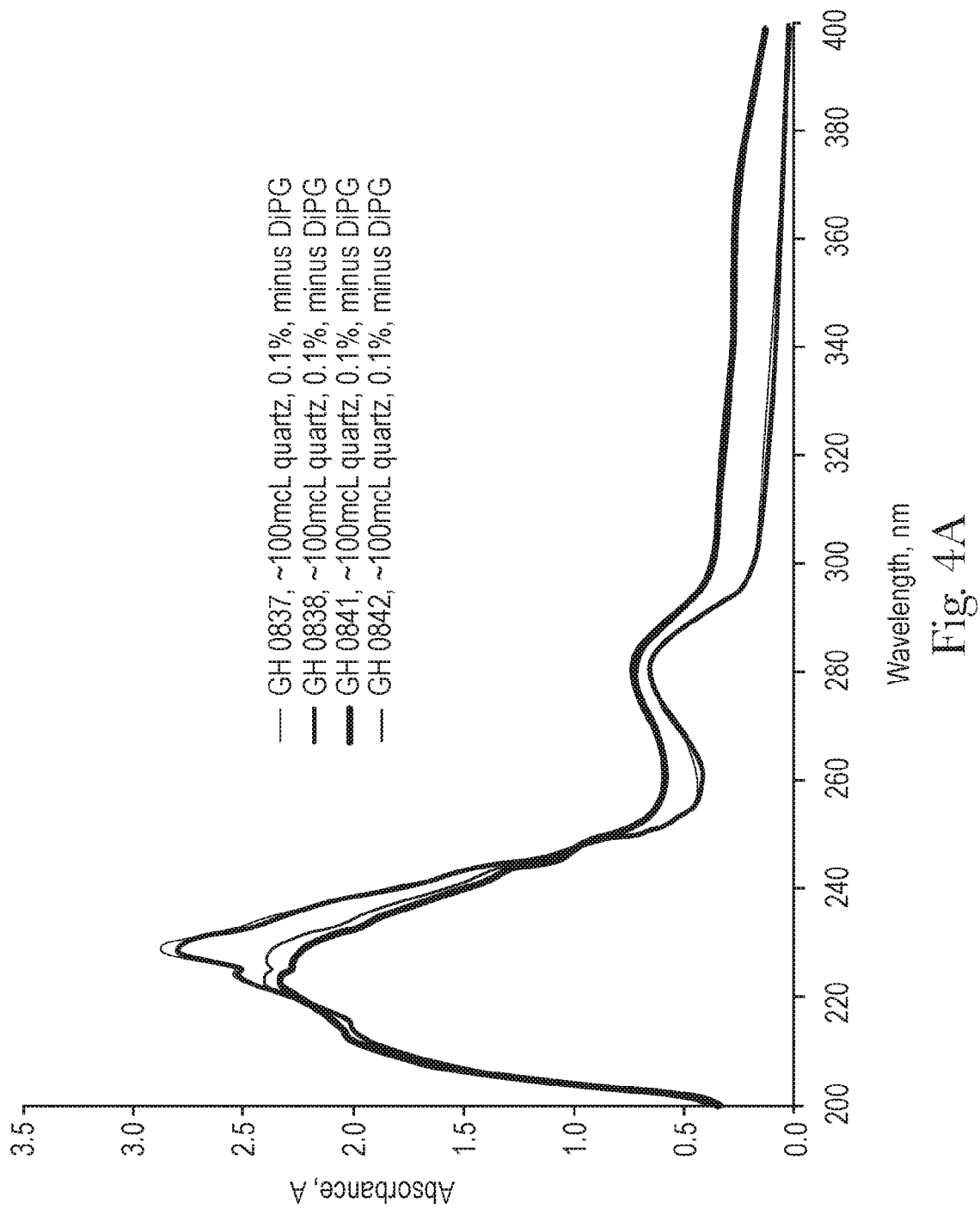

METHOD OF REGULATING A SKIN CONDITION

FIELD

The present invention relates generally to regulating a skin condition with *achachairu*. More specifically, the present invention relates to using *achachairu* serum fractions and/or extracts to regulate a skin condition, for example, by incorporating the fraction or extract into a skin care composition.

BACKGROUND

Human skin is constantly subjected to a variety of insults from extrinsic and intrinsic sources. Extrinsic sources include ultraviolet radiation, environmental pollution, wind, heat, infrared radiation, low humidity, harsh surfactants, abrasives, etc, whereas intrinsic sources include chronological aging and other biochemical changes from within the body. Whether extrinsic or intrinsic, these factors can result in visible signs of damage (e.g., fine lines, wrinkling, hyperpigmentation, sallowness, sagging, dark under-eye circles, puffy eyes, enlarged pores, diminished rate of skin cell turnover, flaking, scaling, dryness, roughness). Currently, there are a number of skin care products available to consumers, the majority of which are directed to delaying, minimizing or even reversing the changes associated with aging skin and/or environmental damage to skin. However, there is a continuing need for products and methods that seek to remedy undesirable skin conditions.

One potential source of bioactive ingredients for regulating conditions in mammalian keratinous tissue is *achachairu*. Achachairu (*Garcinia humilis*) is a plant belonging to the Clusiaceae (or Guttiferae) family and is widely distributed in the region of Santa Cruz, Bolivia. The *achachairu* plant (e.g., fruit) is used in Bolivian folk medicine for its healing, digestive, and laxative properties. In Brazil, *achachairu* is popularly known as "*achacha*" and is used in folk medicine to treat rheumatism, inflammation, pain and gastric disorders (Alves T M A, Silva A F, Brandao M, Grandi T S M, Smania E F et al. (2000) Biological Screening of Brazilian Medicinal Plants. Mem Inst Oswaldo Cruz 95: 367-373 and Barbosa W, Chagas E A, Martins L, Pio R, Tucci M L et al. (2008) "Germinação de sementes e desenvolvimento inicial de plântulas de *achachairu*. Rev Bras Frutic." 30: 263-266).

Some studies suggest that achachar, like many plants, contains unwanted components of concern, such as benzophenones (e.g., guttiferone A) and proteins. See, e.g., Acuña U M, et al., (2009) Polyisoprenylated benzophenones from Clusiaceae: potential drugs and lead compounds. Curr Top Med Chem 9: 1560-1580). Benzophenones are known to exhibit various biological activities such as cytotoxic, genotoxic antimicrobial, antiviral and antioxidant activity. See, e.g., Terrazas P M, et al. (2013) "Benzophenone guttiferone A from *Garcinia achachairu* Rusby (Clusiaceae) Presents Genotoxic Effects in Different Cells of Mice;" PLoS ONE 8(11): e76485). And proteins are known to cause allergic reactions when contacted with skin. See, e.g., V. Janssens, et al., (2015) "Protein contact dermatitis: myth or reality?" British Journal of Dermatology; 132: 1-6). Thus, in some instances it may be desirable to remove these unwanted components or reduce their concentrations substantially when providing an *achachairu* ingredient for incorporation into a skin care composition.

SUMMARY OF THE INVENTION

Disclosed herein is a method of regulating a skin condition, which comprises identifying a target portion of skin in need of treatment or where treatment is desired; and applying an effective amount of *achachairu* serum fraction to the target portion of skin during a treatment period, wherein the treatment period is sufficient for the *achachairu* serum fraction to provide a skin care benefit.

Also disclosed is a method of providing skin care benefit, which comprises identifying a target portion of keratinous tissue in need of treatment; and applying an effective amount of an *achachairu* extract to the target portion of skin during a treatment period, wherein the treatment period is sufficient for the *achachairu* extract to provide a skin care benefit.

BRIEF DESCRIPTION OF THE DRAWINGS

FIGS. 3A, 3B, 4A, 4B are graphs illustrating absorbance spectra of *achachairu* serum fractions and extracts.

DETAILED DESCRIPTION OF THE INVENTION

Figure 1:
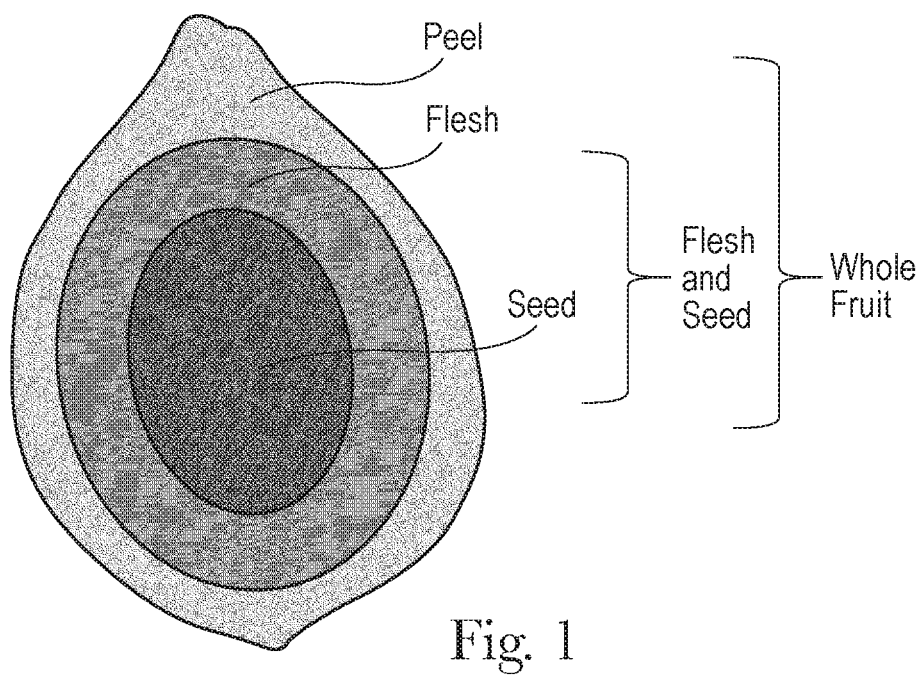
FIG. 1 is a schematic of a cross-sectional view of an *achachairu* fruit.

It has now been discovered that *achachairu* (*Garcinia humilis*), especially bioactive extracts and serum fractions obtained from particular portions of the *achachairu* plant, possess properties that may be beneficial for regulating certain skin conditions. In particular, bioactive *achachairu* fruit extracts and serum fractions exhibit surprising properties related to anti-oxidation, inhibiting melanin production, and inhibiting lipogenesis, which can be exploited to provide a wide variety of different skin health benefits. Thus, it is now possible to regulate a particular skin condition by applying an effective amount of *achachairu* to a target portion of skin where treatment is needed or desired.

It may also be desirable to provide *achachairu* serum fractions and/or extracts that are free or substantially free of benzonphenones (e.g., guttiferone A) and/or proteins. As used herein, "substantially free of proteins" means less than 0.15% total protein content determined by hydrolyzed and un-hydrolyzed amino acid analysis conducted on an Hitachi L-8900 amino acid analyzer or equivalent, and "substantially free of benzophenones" means less than 0.1% total benzophenones, including guttiferone A, as determined by the method described in Dal Molin M M, et al., (2012) "Phytochemical analysis and antinociceptive properties of *Garcinia achachairu* Rusby (Clusiaceae) seeds." Arch Pharm Res 35: 623-631.

As used in the description and the appended claims, the singular forms "a," "an," and "the" are intended to include the plural forms as well, unless the context clearly indicates otherwise. All percentages disclosed herein are by weight of the total composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified. All numeric ranges are inclusive of narrower ranges and combinable; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

Definitions

"About," as used herein, modifies a particular value, by referring to a range equal to the particular value, plus or minus twenty percent (+/−20%) or less (e.g., less than 15%, 10%, or even less than 5%).

"Apply" or "application", as used in reference to a composition, means to apply or spread the compositions of the present invention onto a human skin surface such as the epidermis.

"Derivative" means a molecule similar to that of another one, but differing from it with respect to a certain functional moiety (e.g., esters, ethers, amides, amines, carboxylic acids, hydroxyls, acetyls, thiols, halogens, thiols, and/or salt derivatives of the relevant molecule).

"Dermatologically acceptable" means that the compositions or components described are suitable for use in contact with human keratinous tissue without undue toxicity, incompatibility, instability, allergic response, and the like.

"Effective amount" means an amount of a compound or composition sufficient to significantly induce a positive benefit to skin, such as a health, appearance, and/or feel benefit, including, independently or in combination, the benefits disclosed herein, but low enough to avoid serious side effects (i.e., to provide a reasonable benefit to risk ratio, within the scope of sound judgment of the skilled artisan). An "effective amount" of *achachairu* is an amount of *achachairu* sufficient to regulate a desired skin condition of mammalian keratinous tissue when topically applied thereto in a skin care composition.

"Exogenous solvent" means any solvent placed in contact with the plant material for the purpose of separating compounds from the plant material. It may be a solvent originally present in plant material but added in higher amounts (e.g., in case of water extracts), or a solvent not inherently present in plant material. Plant material herein can include any solid or liquid portion of the *achachairu* plant.

"Extract," when referring to *achachairu*, means a material (e.g., one or more phytochemicals) obtained from a portion of *achachairu* plant material (e.g., peel, fruit, seed, stem, bark, leaves, roots, and/or a combination of these), which may be fresh, dried, or partially dried, by contacting the plant portion(s) with an exogenous solvent and separating the desired material from the solvent using a conventional extraction process. Conventional extraction processes for obtaining plant extracts are well known in the art.

"Regulating a skin condition," as used herein, means improving the health, appearance, and/or feel of skin.

"Salts" refer to ionic forms of a given compound combined with counterions deemed acceptable for a given application (e.g., food, topical, pharmaceutical). Examples include but are not limited to sodium, potassium, calcium, ammonium, manganese, copper, and/or magnesium salts of a given compound.

"Skin care" means regulating and/or improving a skin condition. Some non-limiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improving skin tone, reducing the appearance of redness or skin blotches, and/or improving the brightness, radiancy, or translucency of skin.

"Skin care active" means an active that, when applied to skin, provides an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves a skin condition.

"Topical" refers to a composition that is intended to be applied to a bodily surface such as skin or hair.

Skin Care Composition

The skin care compositions suitable for use in the methods herein include a safe and effective amount of *achachairu* (*Garcinia humilis*). The *achachairu* may be in form of a serum fraction, an extract, a powder, a juice, or a combination thereof. The *achachairu* may be obtained from any part of the *Garcinia humilis* plant, as desired, but it may be particularly desirable to use the *achachairu* fruit or a portion thereof (e.g., peel, pulp, and/or seed). Some testing suggests that the *achachairu* fruit, especially the peel, may contain higher concentrations of biologically active compounds (e.g., carbohydrates, citric acid, flavonoids, xanthones and tannins) than other parts of the *achachairu* plant for regulating particular conditions of mammalian keratinous tissue. The *achachairu* extract and/or serum fraction may be obtained according to the methods described in more detail below and combined with a dermatologically acceptable carrier, along with any optional ingredients, using conventional methods of making skin care compositions. The personal care composition may then be packaged for commercial distribution.

FIG. 1 illustrates the distinct layers and parts of the *achachairu* fruit, as shown by a section passing through a long axis of the fruit. Whole fruit, a particular part of fruit, or any combination of parts of fruit may be used to provide a serum fraction or extract herein.

However, this is not meant to exclude further distinctions of fruit parts than described here, or leaves that may be retained during harvesting. As shown in FIG. 1, the outermost layer of the *achachairu* fruit is the "Peel", which is comparatively thick and tough. The next inward layer is the "Flesh", which is comparatively soft and yielding. The flesh surrounds a comparatively large "Seed". Especially large fruit may have more than one seed.

The amount of *achachairu* that is "effective" can differ from one particular source (e.g., manufacturer) to another, and can be determined by the skilled artisan based upon a particular product's level of activity (e.g., level of active components present). The concentration of active components in the particular *achachairu* product to be used will depend on factors such as the final dilution volume of the product, the particular method employed, the natural range of variation among individual plants, and other common factors known to those skilled in the art. In some instances, an effective amount of *achachairu* may range from 0.01% to 15% (e.g., from 0.1% to 10%, 0.2% to 7%, 0.5% to 5%, or even 1% to 3%).

The skin care compositions herein are intended for topical application to skin, and are formulated accordingly (e.g., have suitable viscosity, color, fragrance, and feel properties). The present skin care compositions may be provided in a variety of forms, including, but not limited to, emulsions, lotions, milks, liquids, solids, creams, gels, mousses, ointments, pastes, serums, sticks, sprays, tonics, aerosols, foams, and/or pencils.

Figure 2:
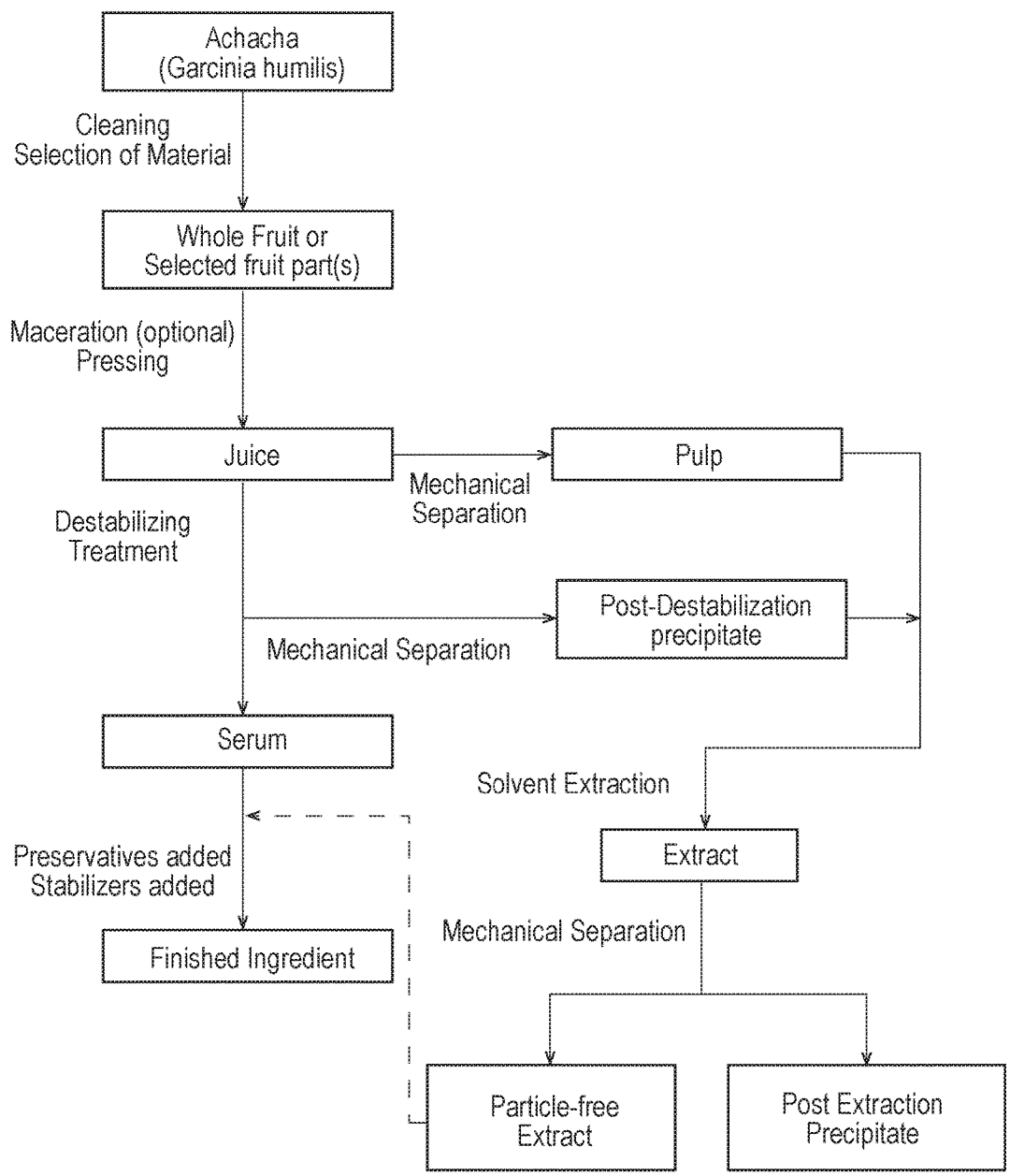
FIG. 2 is a schematic of a process for preparing bioactive serum fractions and bioactive fraction extracts derived from *achachairu*.

FIG. 2 illustrates an exemplary method for providing bioactive *achachairu* ingredients. It is to be appreciated that portions of the process referring to "fruit" can include any portion of the *achachairu* plant, as desired. The individual steps illustrated in FIG. 2 are described in more detail below.

"Cleaning" involves the removal of debris from the harvested *achachairu* plant material, prior to further processing, in a way that avoids injury to the fruit or removal of juice or other desirable components. For example, cleaning can be performed by low-pressure rinsing with potable water, under conditions where residual water wash would not noticeably contain plant pigments.

"Selection of material" involves separating various parts of the *achachairu* plant material to further process a particular part alone, or in combination with other parts. This includes, but is not limited to: selecting whole fruit, peel, flesh, seed and/or leaves for further processing.

"Maceration" is an optional step for rendering the plant material and/or selected parts of the plant material into smaller particles and otherwise disrupting the integrity of the fruit to ease the following expelling of liquid juice. If the selected plant material is especially yielding (such as the flesh of the fruit) or otherwise deemed suitable for conditions and equipment of the pressing step, maceration may be omitted. Examples of suitable maceration implements include, but are not limited to, devices such as a crusher, a grinder, or a mill (e.g., knife mill or hammer mill). To prevent temperature-induced degradation of plant material, maceration can include temperature monitoring and selection of maceration parameters which minimize the risk of temperature increase during this step.

"Pressing" involves the application of mechanical force to the selected, and optionally macerated, *achachairu* plant material to separate at least some of the liquid component from the rest of the plant material. The applied mechanical force may be provided by any suitable means known in the art (e.g., ambient gravity, centrifugal force from a rotary expeller, pressure from the piston of a hydraulic press, or rollers or a screw of appropriate type of press).

"Mechanical separation" involves the removal of relatively large *achachairu* particles (e.g., pulp or agglomerated/aggregated cloud particles) from the liquid component of the *achachairu* plant material.

"Juice" refers to the liquid material expelled from *achachairu* plant material as a result of pressing. Juice can contain solid particles, semi-solid particles, and/or droplets of water-immiscible liquids of a variety of sizes (collectively referred to as "*achacha* particles") in an aqueous serum. *Achachairu* particles, based on size and ease of removal, can be qualitatively described as either "pulp" or "cloud". While details depend on properties of the involved materials (e.g. whole fruit versus selected parts) and exact processing parameters, an example of a size boundary between "pulp" and "cloud" could lie between about 1 and about 100 microns.

"Pulp" refers to relatively large *achachairu* particles present in juice and those same *achachairu* particles removed from the juice by mechanical separation. It is not uncommon to see and distinguish individual pulp particles with a naked eye. Pulp particles suspended in the juice are amenable to removal by mechanical separation, including, but not limited to, sedimentation by ambient gravity, skimming, passing through a mesh or a filter, or centrifugation.

"Cloud" refers to relatively small *achachairu* particles present in the *achachairu* juice, and may even include dissolved compounds (e.g., high molecular weight compounds such as proteins and polysaccharides), which can be readily induced (e.g., by coagulation or temperature change) to form particles. Cloud particles are typically visible as turbidity of the *achachairu* juice, and individual cloud particles are generally indistinguishable to the naked eye. Cloud particles are generally dispersed in the *achachairu* juice and such dispersions tends to remain stable for a longer period time than a pulp suspension, especially colloidal components of the cloud. Removal of cloud particles by mechanical means such as those used for pulp removal can be difficult.

"Destabilizing treatment" generally involves exposing a material to electromagnetic waves in order to modify one or more physical properties of the material (e.g., the real component of low-frequency dielectric constant). With regard to *achachairu* juice, destabilization treatment degrades stability of the particle dispersion in the juice by causing agglomeration and/or aggregation of particles (especially cloud particles) into assemblies that are sufficiently large and stable to enable and/or improve their subsequent removal by mechanical separation techniques such as those described above for pulp removal.

"Serum" refers to liquid portion of *achachairu* juice remaining after pulp and cloud, as well as possible contaminants of concern, has been removed. *Achachairu* serum is free or substantially free of *achachairu* particles.

"Finished ingredient" refers to serum, extract, and/or particle-free extract that is in a form suitable for subsequent sale and/or incorporation into a personal care product. The finished ingredient may include preservatives that protect the serum, extract, particle-free extract, and/or compositions containing the same against environmental challenges such as temperature, atmosphere (e.g., oxygen), light, and microorganisms. It is to be appreciated that an ingredient free of preservatives is also contemplated herein. Surprisingly, it has been found that the processes described herein produce finished ingredients with multifunctional biological activities that are either free of or substantially free of benzophenones and proteins.

"Post-destabilization precipitate" refers to *achachairu* particles removed from the juice via mechanical separation following destabilizing treatment.

"Solvent extraction" in FIG. 2 involves conducting an extraction on *achachairu* particles removed from the *achachairu* juice with one or more solvents (e.g., dipropylene glycol).

The extract shown in FIG. 2 refers to the solution resulting from the solvent extraction of the *achachairu* pulp and post-destablization precipitate. In some instances, any *achachairu* particles remaining in the extract may be separated (e.g., mechanically) to yield a particle-free extract. The extract and/or particle-free extract may serve as a finished ingredient, or as a base for a finished ingredient via addition of preservatives.

"Post-extraction precipitate" refers to *achachairu* particles separated from the extract in FIG. 2.

*Achachairu* Serum Fraction

The compositions herein may include an *achachairu* serum fraction and/or a salt, isomer, or derivative thereof. Serum fraction techniques involve separating the fresh cell juice found in plant material from the rest of the plant matter and processing the juice to provide a stable, refined serum. Examples of *achachairu* serum fractions that may be suitable for use in the compositions and methods herein include Recentia® GH (whole fruit) and Recentia® GH-P (peel only) from Ashland Specialty Ingredients. *Achachairu* peel serum fraction has the INCI designation "*Garcinia humilis* Peel Extract" and the CAS No. 1622986-60-0.

The *achachairu* serum fractions herein may be prepared from fresh *achachairu* using a method that helps maintain the integrity of the bioactive components present in the *achachairu* plant material. Care should be taken to preserve the *achachairu* plant material integrity during harvesting and transport, so as to minimize environmental factors such as moisture loss and biological degradation. All steps of the serum fraction making process should be completed in the shortest possible period of time to minimize exposure of the fresh *achachairu* plant material to sun, high temperature, and other undesirable environmental factors. Harvesting (e.g., by hand or mechanical cutting) should be conducted in a manner that avoids or minimizes the chopping, mashing, crushing, or other type of injury to the *achachairu* plant material to be used (e.g., fruit). Harvest and transport of *achachairu* plant material should be conducted in a manner to avoid moisture loss or spoilage. After harvesting, the *achachairu* plant material (e.g., fruit, leaves) is cleaned to remove debris prior to further processing. Cleaning is performed under conditions to prevent the initiation of the release of the juice from the fruit, to cause injury, or to remove valuable components. For example, the harvested *achachairu* plant material may be washed with water at low-pressure (e.g., 1 kg/cm$^2$ or less) for a short duration (e.g., 5 minutes or less). Excess water is removed from washed fruit biomass before processing.

The washed plant material is processed (e.g., macerated and pressed) to yield juice. In some instances, the whole fruit or a portion thereof (e.g., peel, fruit flesh, and/or seed) is macerated (e.g., by grinding) and then pressed to separate the juice from the rest of the plant matter. For example, a hammer mill may be used to grind the whole fruit to yield plant material particles of a desired size (e.g., less than or equal to 0.5 cm) in a short time (e.g., 10 seconds or less) and without significant increase of biomass temperature (e.g., 5° C. or less). The separation of juice from the *achachairu* plant material is commenced promptly, as soon as possible, after maceration of the *achachairu* plant to avoid a significant increase in temperature of the juice and/or pulp. For example, macerated *achachairu* leaves can be pressed using a horizontal, continuous screw press, wherein the pressure on the cone is maintained at 24 kg/cm$^2$, screw speed is at 12 rpm, and biomass temperature increase is 5° C. or less.

The *achachairu* juice can be subjected to further processing immediately, or the juice may be frozen at about −30° C. and thawed and processed later.

*Achachairu* juice typically contains a variety of *achachairu* particles (i.e., pulp and cloud) in an aqueous serum. Thus, in order to obtain the desired serum fraction, all or substantially all of the *achachairu* particles should be removed from the juice. In some instances, it may be desirable to provide a serum fraction that includes less than 25% dry matter (e.g., less than 20%, 15%, 12%, 10% or even less than 9% dry matter). The pulp may be removed from the *achachairu* juice using a suitable mechanical separation technique such as, for example, straining, filtration (including filtration utilizing a pressure gradient), skimming, sedimentation by ambient gravity, decanting, centrifugation, and/or a combination of these to yield pulp-free or substantially pulp-free juice. The cloud may be removed by exposing the juice to electromagnetic waves to destabilize the cloud dispersion in the juice. The frequency of electromagnetic waves may range between 300 MHz and 50 GHz. Suitable devices for generating such electromagnetic waves include, but are not limited to magnetrons, power grid tubes, klystrons, klystrodes, crossed-field amplifiers, travelling wave tubes, and gyrotrons. In some instances, a magnetron operating at a frequency of 915 MHz, 2.45 GHz, and 5.8 GHz can allow the value of real component of low-frequency dielectric constant ($\varepsilon'_0$) to be decreased during the treatment by between 10 and 40 compared to its value prior to treatment. The value of real component of low-frequency dielectric constant ($\varepsilon'_0$) can be determined using broadband dielectric spectroscopy data obtained via equipment and software from Agilent Technologies: PNA-L Network Analyzer N5230C with 85070E dielectric probe kit, N4693-60001 electronic calibration module, and 85070 software. The calculation is performed according to method described in the article Cole, K. S., & Cole, R. H. (1941). Dispersion and absorption in dielectrics I. Alternating current characteristics. The Journal of Chemical Physics, 9(4), 341-351.

Other non-limiting examples of techniques for providing serum fractions are disclosed in U.S. Pat. Nos. 7,442,391 and 7,537,791 to Koganov and U.S. Pub. No. 2012/0201768, filed by Swanson, et al.

*Achachairu* Extract

The compositions and methods herein may employ an *achachairu* extract. An *achachairu* extract is obtained by separating compounds from *achachairu* plant matter with an exogenous solvent. Consistent with the general principle of "like dissolves like," the choice of extraction solvent largely determines the type and number of compounds that will result from any particular extraction technique. For instance, polar compounds are typically extracted out by using a polar solvent, while non-polar compounds are extracted out by using a non-polar solvent. The correlation between solvent polarity and the types of materials isolated using traditional solvent extraction is described in Houghton & Raman, *Laboratory Handbook for the Fractionation of Natural Extracts* (1998).

The *achachairu* extracts herein may be obtained using any suitable extraction technique known in the art. In some instances, the *achachairu* extract may be obtained by the following procedure: (i) place the desired portion of dried plant material (e.g., whole fruit, fruit pulp, peel, seeds, stem, bark, leaves) in a conical glass percolator; (ii) add the indicated percentage of extraction solvent in a w/w ratio of 1 part plant material to 2 parts extraction solvent (when the indicated percentage of extraction solvent is less than 100%, the remaining solvent is water (e.g., 95% ethanol with 5% water, 50% ethanol with 50% water)); (iii) allow the extraction to proceed for 16 to 24 hours; (iv) collect the percolate, and repeat the above process until the resulting percolate is substantially free from plant additional extract; (v) combine the percolates, evaporate to dryness under reduced pressure, and store the resulting extract under nitrogen at less than 4 degrees Celsius. Extracts may be used without any further modification or may be modified (e.g., ethoxylated, esterified) to form a derivative material.

Achachairu Powder or Juice

The personal care compositions for use with the methods herein may include an *achachairu* powder or juice. *Achachairu* juice may be obtained by macerating and process *achachairu* plant material, for example, as described hereinabove. *Achachairu* powder may be obtained by drying *achachairu* plant material and processing the dried material into particles. Additionally or alternatively, the *achachairu* plant material may be processed into particles and then dried. Processing the *achachairu* into particles may include one or more grinding steps performed before and/or after drying. The *achachairu* biomass may be dried and processed into particles using any suitable method known in the art. The *achachairu* powder may have a weight average particle size of from 50 to 750 microns. Once the *achachairu* is processed into particles of the desired size, the powder can be incorporated into a personal care composition using conventional methods for making such compositions.

Dermatologically Acceptable Carrier

The skin care compositions herein include a dermatologically acceptable carrier at an amount of 20% to 99.99% (e.g., 50% to 99%, 60% to 98%, 70% to 95%, or even 60% to 80%) by weight of the composition. The carrier may be aqueous or anhydrous. The form of the carrier is not particularly limited, and can be any suitable form known in the art for the application desired (e.g., solutions, dispersions, emulsions and combinations thereof). "Emulsions" refer to compositions having an aqueous phase and an oil phase. Emulsion carriers include, but are not limited to oil-in-water, water-in-oil and water-in-oil-in-water emulsions. Emulsion carriers herein may include from 0.01% to 10% (e.g., 0.1% to 5%) of an emulsifier (e.g., nonionic, anionic, cationic emulsifier, or a combination thereof). Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986).

Optional Ingredients

The compositions of the present invention may contain a variety of optional ingredients that are conventionally used in skin care compostions, as long as the optional ingredient(s) do not undesirably alter product stability, aesthetics or performance The optional ingredients, when incorporated into the composition, should be suitable for contact with human skin without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients. The compositions herein may include 0.0001% to 50%; from 0.001% to 20%; or even 0.01% to 10%, by weight of the composition, of optional ingredients. Some non-limiting examples of optional ingredients include vitamins, minerals, peptides and peptide derivatives, sugar amines, oil control agents, flavonoid compounds, anti-oxidants and/or anti-oxidant precursors, preservatives, phytosterols, protease inhibitors, tyrosinase inhibitors, anti-inflammatory agents, moisturizing agents, emollients, humectants, exfoliating agents, skin lightening agents, sunscreens, sunless tanning agents, pigments, film formers, thickeners, pH adjusters, opacifying agents, colorings/colorants, particles, fragrances, essential oils, lubricants, anti-acne actives, anti-cellulite actives, chelating agents, anti-wrinkle actives, anti-atrophy actives, phytosterols and/or plant hormones, N-acyl amino acid compounds, antimicrobials, antifungals, and combinations of these. Other non-limiting examples of skin care actives can be found in U.S. Pub. Nos. 2010/0272667 and 2008/0206373 and U.S. Pat. No. 8,790,720.

Methods of Regulating a Skin Condition

Skin care compositions comprising an effective amount of *achachairu* can be used to regulate a skin condition by topically applying the skin care composition to a portion of mammalian tissue in need of treatment or where treatment is desired. Identifying a target portion of skin may be based on, for example, the presence of a visible condition (e.g., dryness, undesirable feel, redness, inflammation, discoloration, or wrinkles). In some instances, the target portion of skin may not exhibit visible signs of a skin condition, but a user may still wish to target such an area if it is one that is known to develop a condition (e.g., skin surfaces that are typically not covered by clothing).

Skin care compositions containing an effective amount of *achachairu* may be applied once a day, twice a day, or on a more frequent daily basis, during a treatment period. The treatment period is ideally of sufficient time for the *achachairu* to provide the desired benefit. For example, the treatment period may be of sufficient time for the *achachairu* to provide a noticeable and/or measurable improvement in a hair or skin condition. The treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, a cosmetic composition containing an effective amount of *achachairu* may be applied most days of the week (e.g., at least 4, 5 or 6 days a week), at least once a day or even twice a day during a treatment period of at least 2 weeks, 4 weeks, 8 weeks, or 12 weeks.

The skin care compositions herein may be applied locally or generally. In reference to application of the composition, the terms "localized", "local", or "locally" mean that the composition is delivered to the targeted area while minimizing delivery to skin surfaces where treatment is not needed or desired. While certain embodiments herein contemplate applying a composition locally to an area, it will be appreciated that the compositions herein can be applied more generally or broadly to one or more skin surfaces. In certain embodiments, the compositions herein may be used as part of a multi-step beauty regimen, wherein the present composition may be applied before and/or after one or more other compositions.

Using the skin care compositions herein according to the present methods can provide a skin benefit. Some non-limiting examples of skin benefits include reducing the appearance of wrinkles, deep lines, fine lines, crevices, bumps, large pores; increasing the convolution of the dermal-epidermal border; skin lightening; increasing elasticity, decreasing sagging, reducing cellulite; reducing the appearance of under-eye circles, reducing the appearance of discoloration, reducing hyperpigmentation, increasing skin luminosity, and combinations thereof.

The skin care compositions may be applied by any suitable means known for applying such products, including rubbing, wiping or dabbing with hands, fingers and/or an implement. Non-limiting examples of implements include a sponge or sponge-tipped applicator, a swab (for example, a cotton-tipped swab), a pen optionally comprising a foam or sponge applicator, a brush, a wipe, and combinations thereof. The composition may be pre-applied to the applicator and, for example, delivered to the user pre-packaged as such, or the user may be instructed to apply the composition to the applicator prior to use. In some instances, the composition may be stored in an implement, for example, in a separate storage area for the composition. In this example, the composition may be transferred to the applicator from the storage area, for example, by squeezing and/or breaking or by other suitable means. The composition may be applied to the keratinous tissue by contacting the applicator and composition to the skin. Contact may include, for example, light pressure, dabbing, rubbing, wiping, or any other suitable means. When targeted application is desired, the composition may be applied to the desired area of keratinous tissue.

Methods for Determining the Effectiveness of *Achachairu*

Irritation and inflammation in human skin can lead to visible signs of skin aging (e.g. discoloration and wrinkles), decreased mechanical strength, decreased protective functions, and lessened ability to recover from stress and injuries. Ubiquitous stressors such as sunlight and surfactants can be especially problematic. Mitigating irritation and inflammation of the skin, particularly those caused by common stressors, is important and desirable.

The adverse effects of light, most commonly sunlight (though artificial sources are included), on human skin are well known. Overly high exposure to sunlight may cause acute adverse reaction involving irritation and inflammation, such as sunburn. Exposures insufficient to cause acute reactions can still trigger inflammation-related processes. Accumulated inflammatory damage from sunlight exposure causes degradation of skin resilience and development of an undesirable appearance (i.e., photoaging).

Surfactants are also known to cause adverse reactions on human skin. Surfactants are used in a variety of personal care and cleansing products to allow or improve processes of cleansing, foaming, emulsifying, solubilizing, and dispersing. Repetitive contact with surfactant-containing products has been shown to cause damage of the skin barrier due to surface or interface activities of the surfactants, which can be perceived by consumers as dryness, itchiness, swelling, redness, and/or pain. The weakened barrier subsequently leads to deeper penetration of the surfactants into skin and induced irritation and inflammation. As surfactants are widely used in hand soaps, facial and body washes, shampoos and conditioners, as well as dish, laundry and housecleaning detergents, human skin contact with surfactants is common.

Irritation and inflammation are commonly viewed as a "cascade" proceeding from necessary release of a signaling compound Interleukin (IL) 1-alpha (or IL-1α) to induction of other downstream cytokines and chemokines such as interleukins IL-6 and IL-8 or other signaling molecules (Weiss T, Basketter D A, Schröder K R. In vitro skin irritation: facts and future. State of the art review of mechanisms and models. Toxicol In Vitro 2004; 18 (3): 231-43). However, previously published data suggest that "cascade" view might not be a comprehensive model.

It has been shown that sodium dodecyl sulfate (SDS), a single compound commonly used as a benchmark source of surfactant stress in both in vitro and in vivo studies, can trigger different portions of the irritation and inflammation process without significantly affecting release of a primary cytokine such as IL-1α, depending on concentration. The complexity of irritation and inflammation response of skin cells implies that signaling "network" model is a more adequate analogy than a signaling "cascade" model. This indicates that mitigation of such a complex signaling process must affect more than one pathway, such as by using a multifunctional bioactive ingredient.

One of the methodologies for studying and quantifying irritation and inflammation includes culturing cells of the tissue most likely to come in contact with stress sources, such as viable epidermal keratinocytes from human skin. Human epidermal keratinocytes (HEK) have become the focus of attention in irritant-induced skin inflammation by virtue of their epidermal location, importance in maintaining the integrity of the stratum corneum barrier, and the ability to produce a variety of inflammatory mediators. Keratinocytes can release a variety of signalling substances (e.g., interleukins and arachidonic acid metabolites) in response to a range of irritants, including surfactants and sunlight. The amounts of these signalling substances present in a tissue sample can be measured via techniques such as Enzyme-Linked Immunosorbent Assay (ELISA). Bioactive substances that reduce the release of inflammatory signalling substances may help control the signs of irritation and inflammation in human skin.

Besides signalling substances, other very important compounds in processes of irritation and inflammation are those that directly cause the damage. Especially notable inflammatory damage substances are free radicals (especially reactive oxygen species) and protein-degrading enzymes (proteases). It is possible to detect the presence or measure the activity of such damaging substances by incubating them with a substrate they can alter or degrade. The alteration or degradation of the substrate can be measured directly (e.g., by loss or development of color or fluorescence) or indirectly (e.g., by ELISA). In some cases, the presence or activity of damaging substances can be measured directly or indirectly, for example, with spectroscopic techniques (e.g., Electron Paramagnetic Resonance techniques and the use of chromogenic artificial stable free radicals like DPPH).

The tests selected for determining the effects of serum fractions and extracts of *achachairu*, and skin care compositions containing the same, include inhibition of proteases (damaging compounds) in non-cell-based bioassays, inhibition of chemokines, cytokines and prostaglandins (signalling compounds) in cultured human skin cells, inhibition of a compound capable of both signalling and causing damage in cultured human cells, and measuring release or lack thereof of substances indicating cell damage or sensitization. These tests illustrate safety (e.g., via a lack of cytotoxicity and sensitization potential) and the efficacy and potency of *achachairu* in inhibiting signalling and damaging compounds involved in skin irritation, inflammation, and aging processes. The cells in the assays described herein are normal human adult epidermal keratinocytes (HEK), unless specifically stated otherwise.

EXAMPLES

The following examples are provided for the purpose of illustration only and should in no way be construed as being limiting, but rather should be construed to encompass any and all variations which become evident as a result of the teaching provided herein.

Example 1—Preparation of a Serum Fraction from *Achachairu* Whole Fruit

In this example, *achachairu* (*Garcinia humilis*) whole fruit are used to produce a serum fraction. The *achachairu* fruit are harvested fresh from trees, inspected, and cleaned prior to processing. Unsound fruit is not used. Selected whole fruit are ground, pressed, and mechanically separated to provide juice and pulp. The yield of juice from *achachairu* whole fruit after grinding, pressing and mechanical separation is about 60 to 69% weight/weight; the pH of juice from *achachairu* whole fruit is from 3.0 to 3.3. The juice is immediately subjected to destabilizing treatment by electromagnetic waves in a continuous flow system that includes magnetrons operating at a frequency of 5.8 GHz. The parameters of the electromagnetic waves in the destabilization step are set to achieve the decrease in value of real component of low-frequency dielectric constant (E) during the treatment by about 20 Farads per meter (F/m) compared to its value prior to treatment. The de-stabilized juice is immediately pumped through a continuous flow centrifuge to yield a serum and post-destabilization precipitate. The serum is substantially free of benzophenones and protein.

Example 2—Preparation of Serum Fraction from *Achachairu* Peel

In this example, *achachairu* fruit peel is used to produce a serum fraction. The *achachairu* fruit are harvested fresh from trees, inspected, and cleaned prior to processing. Unsound fruit is not used. The fruit peel is separated from whole fruits and then ground, pressed, and mechanically separated to produce juice and pulp. The yield of juice from *achachairu* fruit peel after grinding (maceration), pressing and mechanical separation is about 25 to 35% weight/weight; the pH of juice from *achachairu* fruit peel is 2.7 to 3.0. The juice from fruit peel is immediately subjected to destabilizing treatment by electromagnetic waves in a continuous flow system that includes magnetrons operating at a frequency of 2.45 GHz. The parameters of the electromagnetic waves in the destabilization step are set to achieve the decrease in value of real component of low-frequency dielectric constant ($\varepsilon'_0$) during the treatment by about 30 Farads per meter (F/m) compared to its value prior to treatment. The de-stabilized juice is immediately pumped through a continuous flow centrifuge to yield a serum and post-destabilization precipitate. The serum is free or substantially free of benzophenones and protein.

Example 3—Preparation of Serum Fraction from *Achachairu* Fruit Flesh and Seeds In this example, *achachairu* fruit flesh and seeds are used to produce a serum fraction. The *achachairu* fruit are harvested fresh from trees, inspected, and cleaned prior to processing. Unsound fruit is not used. The fruit flesh and seed are separated from whole fruits and then ground, pressed and mechanically separated to produce juice and pulp. The yield of juice from *Achachairu* (*Garcinia humilis*) fruit flesh and seeds after grinding, pressing and mechanical separation is about 30 to 40% weight/weight; the pH of juice from *achacha* fruit flesh and seeds is 3.8 to 4.2. The juice is immediately subjected to destabilizing treatment by electromagnetic waves in a continuous flow system that includes magnetrons operating at a frequency of 2.45 GHz. The parameters of the electromagnetic waves in the destabilization step are set to achieve the decrease in value of real component of low-frequency dielectric constant ($\varepsilon'_0$) during the processing by about 25 Farads per meter (F/m) compared to its value prior to treatment. The de-stabilized juice is immediately pumped through a continuous flow centrifuge to yield a serum and post-destabilization precipitate. The serum is free or substantially free from benzophenones and protein.

Example 4—Preparation of Extracts from *Achachairu* Fruit by Solvent Extraction Solvent extractions were conducted with pulp particles, with post-destabilization precipitate particles, including cloud, or with their combination using one or more solvents under particular extraction conditions: type of solvent(s), ratio of solvent to plant material (pulp, or post-destabilization precipitate, or their combinations), extraction temperatures, agitation, time of exposure, etc., in order to extract materials that are soluble in the particular solvents. The ratio of pulp and/or post-destabilization precipitate to solvent can range from 1:2 to 1:1000. Extraction temperature can range from 4° C. to 100° C. Time of the exposure may vary from about 15 minutes to about 96 hrs.

Example 5—Skin Care Composition Formulations

Table 1 provides examples of topical skin care compositions comprising *achachairu*. The compositions in Table 1 are made by blending the A phase components with a suitable mixer (e.g., Tekmar RW20DZM) and heating to a temperature of 70-80° C. and maintaining the temperature while stirring. Separately, blend the B phase components with a suitable mixer and heat to 70-75° C., maintaining temperature while mixing. Phase B is added to Phase A while mixing well to emulsify. The emulsion is then milled using a suitable mill (e.g., Tekmar T-25) for 5 minutes. When the emulsion is at 60° C., phase C is added while continuing to mix. At 40° C., the ingredients of phase D and E are added to the emulsion. The emulsion is then milled using a suitable mill (Tekmar T-25) for 5 minutes resulting in a uniform product.

TABLE 1

| Component | Ex. 1 | Ex. 2 | Ex. 3 | Ex. 4 % | Ex. 5 | Ex. 6 | Ex. 7 |
|---|---|---|---|---|---|---|---|
| Phase A | | | | | | | |
| water | qs | qs | qs | qs | qs | qs | qs |
| glycerol | 5.00 | 7.00 | 3.00 | 10.00 | 5.00 | 5.00 | 5.00 |
| disodium EDTA | 0.10 | 0.05 | 0.10 | 0.10 | 0.10 | 0.10 | 0.10 |
| Phase B | | | | | | | |
| Isopropyl Isostearate | 5.00 | 2.50 | 1.33 | 2.50 | 5.00 | 5.00 | 5.00 |
| Isohexadecane | 1.00 | 1.50 | 3.00 | 1.00 | 1.00 | 1.00 | 1.00 |
| Distearyldimonium Chloride | 0.00 | 0.50 | 1.00 | 1.50 | 0.00 | 0.00 | 0.00 |
| Steareth-2 | 0.50 | 2.00 | 1.00 | 1.00 | 0.50 | 0.50 | 0.50 |
| cetyl alcohol | 0.25 | 0.50 | 0.32 | 0.50 | 0.25 | 0.25 | 0.25 |
| tocopherol acetate | 0.00 | 0.50 | 0.50 | 0.50 | 0.00 | 0.00 | 0.00 |
| Steareth-21 | 0.50 | 1.00 | 0.40 | 0.80 | 0.50 | 0.50 | 0.50 |
| stearyl alcohol | 0.70 | 1.50 | 2.00 | 2.25 | 0.70 | 0.70 | 0.70 |
| behenyl alcohol | 0.80 | 1.00 | 0.40 | 0.60 | 0.80 | 0.80 | 0.80 |

TABLE 1-continued

| Component | Ex. 1 | Ex. 2 | Ex. 3 | Ex. 4 % | Ex. 5 | Ex. 6 | Ex. 7 |
|---|---|---|---|---|---|---|---|
| ethyl paraben | 0.20 | 0.20 | 0.20 | 0.20 | 0.20 | 0.20 | 0.20 |
| propyl paraben | 0.10 | 0.10 | 0.10 | 0.10 | 0.10 | 0.10 | 0.10 |
| polymethyl-silsesquioxane | 1.25 | 2.50 | 2.00 | 0.50 | 1.25 | 1.25 | 1.25 |
| Phase C | | | | | | | |
| Polyethylene | 1.50 | 1.00 | 1.50 | 2.00 | 1.50 | 1.50 | 1.50 |
| Phase D | | | | | | | |
| Water | 5.00 | 10.00 | 10.00 | 5.00 | 5.00 | 5.00 | 5.00 |
| Achachariu serum fraction | 0.1 | 0.5 | 2.0 | 10.0 | — | — | — |
| Achachariu extract | — | — | — | — | 0.1 | 0.5 | 2 |
| dexpanthenol | 0.25 | 0.50 | 0.50 | 2.00 | 0.25 | 0.25 | 0.25 |
| Phase E | | | | | | | |
| benzyl alcohol | 0.25 | 0.25 | 0.25 | 0.25 | 0.25 | 0.25 | 0.25 |
| dimethicone/dimethiconol | 0.5 | 1.00 | 2.00 | 0.25 | 0.5 | 0.5 | 0.5 |

Example 6—Preservatives

Various preservatives were tested for use with the bioactive serum fractions and bioactive extracts of *achacha* herein. Table 2 shows an example of combination/concentrations of preservatives that may be particularly for preparing finished *achacha* ingredients (e.g., prepared from the serum fractions described in Examples 1, 2, and 3). It has been found that the preservatives listed in Table 2 help prevent the formation of precipitates in a finished product.

TABLE 2

| Preservative | Amount (wt %) |
|---|---|
| Pentylene Glycol (CAS 5343-92-0) | 1.90% |
| Tetrasodium EDTA (CAS 64-02-8) | 0.25% |
| Sodium metabisulfite (CAS 7681-57-4) | 0.20% |
| Potassium sorbate (CAS 590-00-1) | 0.10% |
| Sodium Benzoate (CAS 532-32-1) | 0.10% |
| Bioactive Serum Fraction or Extract | 97.45% |

Example 7—Physico-Chemical Characteristics

Table 3 illustrates methods for testing and evaluating certain physico-chemical characteristics of *achacha* serum fractions and extracts. It is to be appreciated that the methods are not limited to the specific instruments or techniques shown, and equivalent instruments and techniques may be used to achieve substantially the same results, as known by those skilled in the art.

TABLE 3

| Property | Test Method | Units |
|---|---|---|
| Appearance | Determined organoleptically. | N/A |
| Odor | Determined organoleptically. | N/A |
| Color | Determined on Lovibond Comparator 3000 Gardner Scale. Turn on comparator lamp. Measure 8 mL of sample into sample tube. Insert tube into comparator. Rotate the knobs until two color standards nearest in color to the sample have been located. Record the value of the sample color accordingly. If the color of the sample is substantially similar to both, rather than a single standard, then record it as a value between the values of the two standards. | Gardner scale |
| Dry Matter | Dry matter is determined by comparing the weights of liquid sample with residual dry matter after water has been evaporated. Procedure is based on standard laboratory practices commensurate with available equipment. Select a suitable aluminum weighing dish (e.g., VWR 25433-016) and weight the dish. Add approximately 4 mL of liquid sample to the dish with the dish on the scale. Determine the weight of the liquid sample by subtracting the dish weight from the total weight. Repeat this procedure with two additional weighing dishes. Place the dishes in a ThermoScientific "Lindberg Blue M" Gravity oven at 105 degrees Celsius for 24 hours. After 24 hours, remove the dishes and allow them to cool for approximately 5 minutes at room temperature. Weigh each dish. Determine the weight of the dry sample. Calculate dry matter percentage by dividing dry sample weight by liquid sample weight. Dry matter percentage for the sample is the average of the dry matter percentages for the three dishes. | % |
| Refractive index | Determined using a Reichert Arias™ 500 brand refractometer according to instruction manual sections 6.0, 4.1 and 4.4-4.5. Temperature regulation is provided by Cole-Parmer Polystat temperature controller, model number 12108-10 set at 20 C. Automatic Reading Method is enabled. Place 0.5 mL of deionized water on the surface of the lower measuring prism, taking care to avoid bubble formation. Close the cell and turn the shadowline adjustment knob to bring the shadowline within the crosshairs. Wait for temperature at refractometer measuring cell to stabilize, then push Read button. Repeat until refractive index of deionized water is determined as 1.333 at least three times in a row. Rinse the lower and upper surfaces of the | nD |

TABLE 3-continued

| Property | Test Method | Units |
|---|---|---|
| | measuring cell with deionized water and blot dry with lint-free wipe. Place 0.5 mL of sample on the surface of the lower measuring prism. Close the cell and turn the shadowline adjustment knob to bring the shadowline within the crosshairs. Wait for temperature at refractometer measuring cell to stabilize, then push Read button. Repeat until stable readings have been obtained for sample material at least three times in a row. Record this value as the Refractive Index. | |
| Density | Determined with Densito 30PX densitometer from Mettler Toledo. Procedure is based on Operating Instructions for Densito 30PX, sections 4 and 6. Set the instrument display to $g/cm^3$. Calibrate the instrument with 4 $cm^3$ of deionized water, avoiding bubble intake or formation. If the density of the calibration sample deviates by more than 0.05% from the expected density of water at ambient temperature, recalibrate the densitometer as per Operating Instructions. Eject the calibration sample and fill the sample loops with 4 $cm^3$ of sample, avoiding bubble intake or formation. Record the reading. Eject the sample and repeat steps above for additional readings, until receiving three matching readings in a row. Record the value of density (specific gravity) for the sample. | $g/cm^3$ |
| pH | Determined by measuring on a Denver Instrument Model 250 pH/ISE/conductivity meter with pH/ATC electrode number 300729.1. Procedure is based on manufacturer's 301127.1 Rev. D manual, pages ii and 9 through 12. Use pH 4.01 and pH 7.00 buffers to calibrate the pH meter. | N/A |
| Total Plate Count | Determined as per US Pharmacopoeia XXX, NF25, <61>, Microbiological Limit Tests | CFU/gm |
| Mold/Yeast | Determined as per US Pharmacopoeia XXX, NF25, <61>, Microbiological Limit Tests | CFU/gm |
| *E. coli* | Determined as per US Pharmacopoeia XXX, NF25, <61>, Microbiological Limit Tests | CFU/gm |
| *Salmonella* sp. | Determined as per US Pharmacopoeia XXX, NF25, <61>, Microbiological Limit Tests | CFU/gm |
| *Staphylococcus aureus* | Determined as per US Pharmacopoeia XXX, NF25, <61>, Microbiological Limit Tests | CFU/gm |
| *Pseudomonas* sp. | Determined as per US Pharmacopoeia XXX, NF25, <61>, Microbiological Limit Tests | CFU/gm |
| Benzophenones, | Dal Molin MM, Silva S, Alves DR, Quintão NLM, Delle Monache F et al.(2012) Phytochemical analysis and antinociceptive properties of *Garcinia achachariu* Rusby (Clusiaceae) seeds. Arch Pharm Res 35: 623-631. | % |
| Protein | Amino acid analysis conducted on Hitachi L-8900 amino acid analyzer according the manufacturer's instructions. | % |

Some physico-chemical characteristics of the present *achacha* serum fractions and extracts are illustrated in Tables 4, 5, and 6 below. The serum fractions and extracts are prepared according to the methods described in the corresponding example(s) above. The *achacha* serum fraction included in the finished ingredient Recentia® GH-P (CAS RN#1622986-60-0), which is illustrated in Table 6 below, is prepared according to the process described in Example 2.

TABLE 4

| | Serum Fractions | | |
|---|---|---|---|
| | Serums obtained from: | | |
| | Whole Fruit Lot GH 0785 | Fruit Peel Lot GH 1082 | Fruit Flesh and Seed Lot GH 1083 |
| Appearance | Clear Orange Liquid | Clear Orange Liquid | Hazy Yellow Liquid |
| Odor | Characteristic | Characteristic | Characteristic |
| Color (Gardner Scale) | 6.5 | 8.5 | 6.5 |
| Dry matter (%) | 13.05 | 11.02 | 16.3 |
| Refractive index (nD) | 1.355 | 1.352 | 1.359 |
| pH | 3.06 | 2.85 | 4.03 |
| Density, $g/cm^3$ | 1.0612 | 1.0514 | 1.0714 |
| Protein | <0.07% | <0.13% | <0.15% |
| Benzophenones | <0.1% | <0.1% | <0.1% |

TABLE 5

Extracts

Extracts (1 part plant material + 3 part solvent ratio, weight/weight) obtained from:

|  | Whole Fruit Extracted at 4° C. Lot. GH 0841 | Fruit Peel Extracted at 4° C. Lot GH (PE) 0837 | Whole Fruit Extracted at 40° C. Lot. GH 0842 | Fruit Peel Extracted at 40° C. Lot GH (PE) 0838 |
|---|---|---|---|---|
| Appearance | Orange Liquid | Orange Liquid | Orange Liquid | Orange Liquid |
| Odor | Characteristic | Characteristic | Characteristic | Characteristic |
| Color (Gardner Scale) | 11.0 | 12.5 | 11.5 | 13.5 |
| Refractive index (nD) | 1.4315 | 1.4291 | 1.4314 | 1.4291 |
| Protein | <0.046% | <0.049% | <0.041% | <0.046% |
| Benzophenones | About 0.1% | <0.1% | About 0.1% or higher | <0.1% |

TABLE 6

Recentia ® GH-P

| Test Parameter | Result |
|---|---|
| Appearance | Clear Orange Liquid |
| Odor | Characteristic |
| Solubility in water | Soluble in any ratio |
| Color (Gardner scale) | 5-12 |
| Dry matter (%) | 9.0-12.1 |
| pH | 2.9-3.8 |
| Refractive index (nD) | 1.349-1.355 |
| Total Plate Count (CFU/g) | <100 |
| Mold/Yeast (CFU/g) | <100 |
| E. coli (CFU/g) | Negative/10 g |
| Salmonella sp. (CFU/g) | Negative/10 g |
| Staphylococcus aureus (CFU/g) | Negative/10 g |
| Pseudomonas sp. (CFU/g) | Negative/10 g |

Example 8—Absorbance Spectra

Figure 3A:
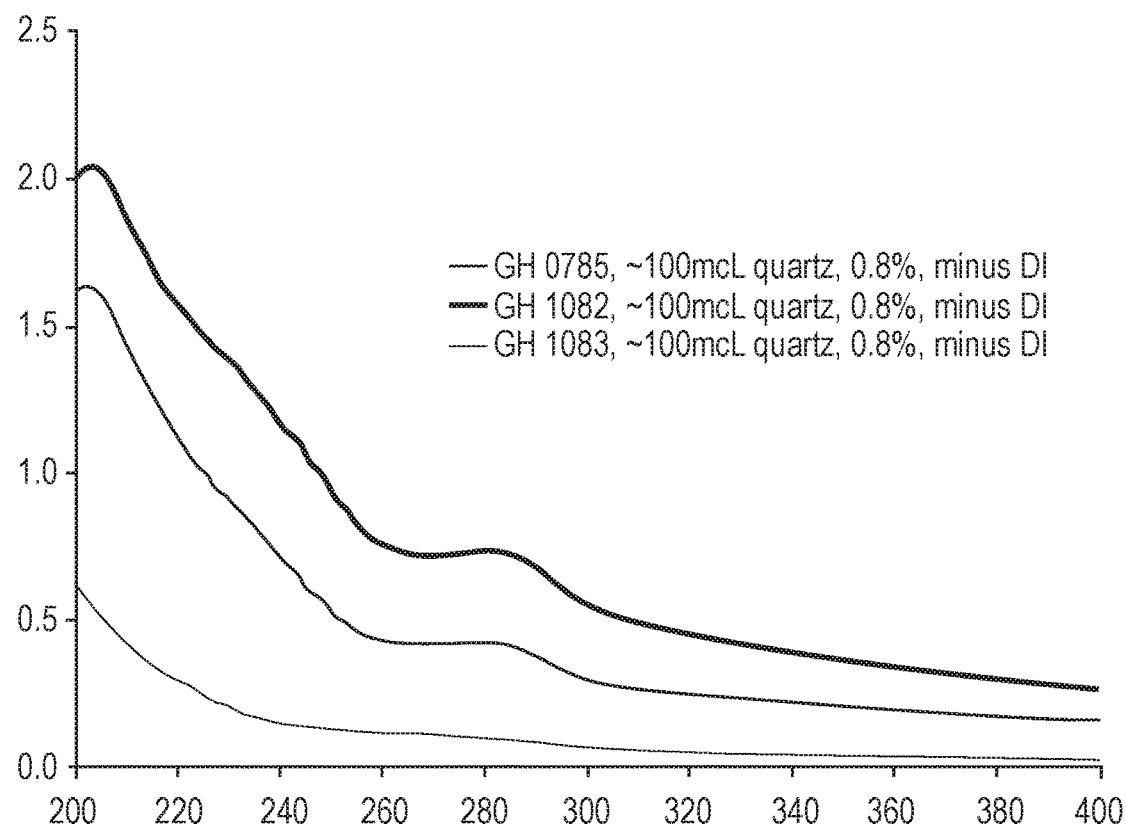
Figure 3B:
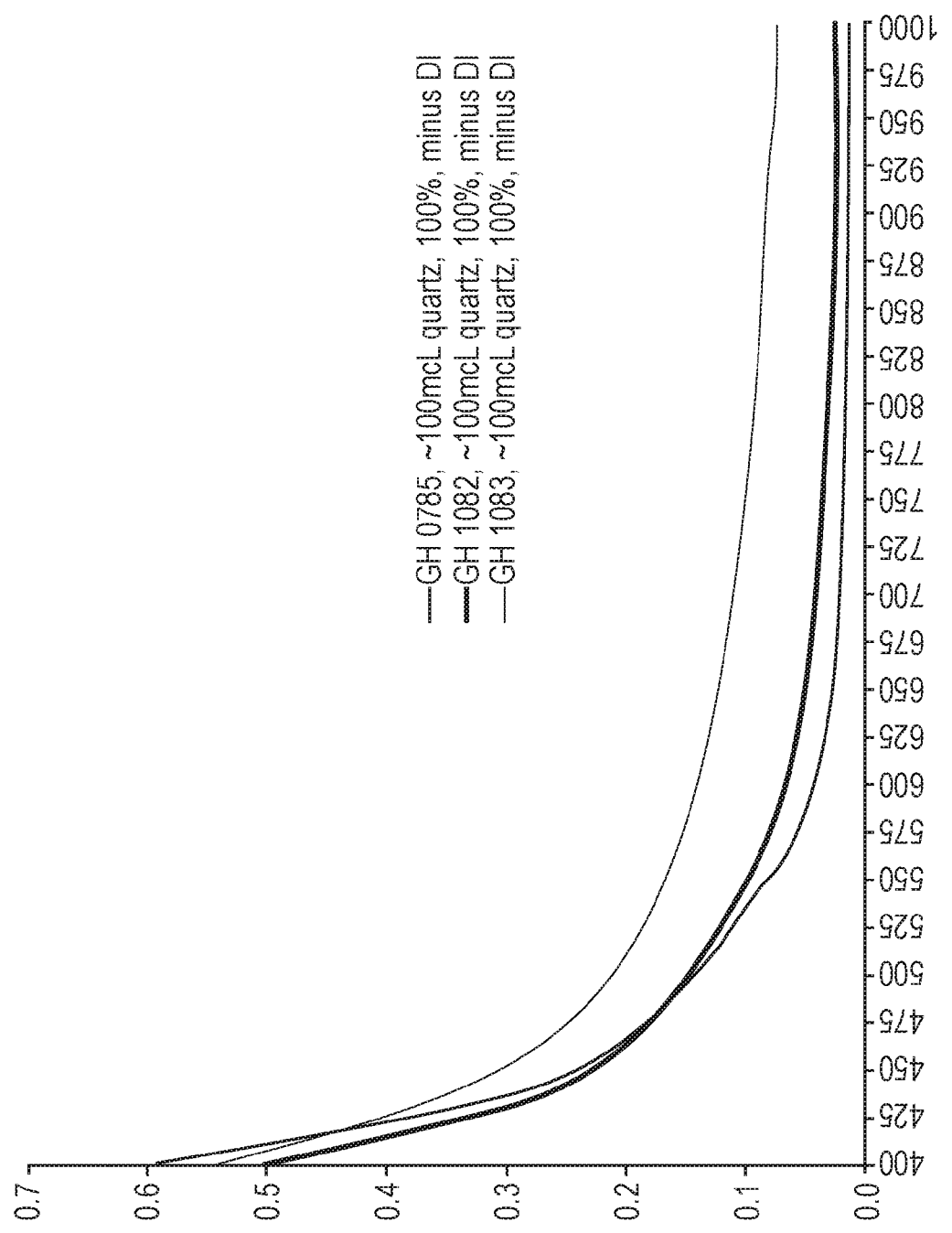
Figure 4B:
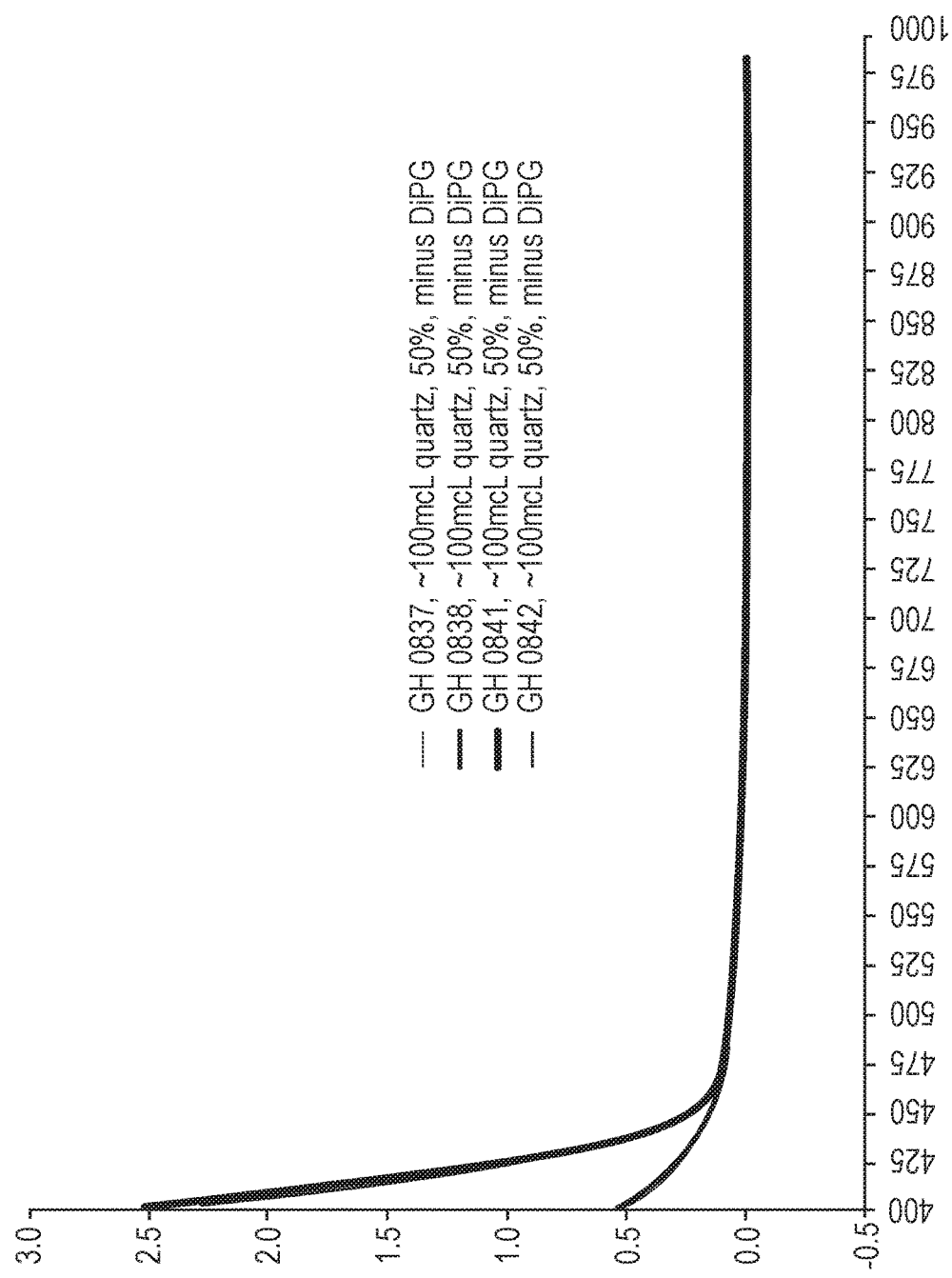

Absorbance spectra (in wavelength ranges 200-400 nm and 400-1000 nm) were obtained from 100 microliter samples of serum fractions and extracts of *achachairu* using a Synergy 2 multi-mode microplate reader (BioTek Instruments, Inc) with 96-well black quartz microplate (Hellma Analytics GmbH). All dilutions were done as volume/volume. Spectra of 100 microliter aliquots of respective solvents (ultrapure deionized water and fragrance grade dipropylene glycol) were subtracted from sample spectra. A summary of the absorbance spectra results are illustrated in FIGS. 3A, 3B, 4A, and 4B. FIGS. 3A and 4A illustrate absorbance spectra of a wavelength range of 200-400 nm. The samples of *achacha* serum fractions and extracts analyzed in FIGS. 3A and 3B included GH 0785, GH 1082, and GH 1083. The samples of *achacha* serum fractions and extracts analyzed in FIGS. 4A and 4B included GH 0837, GH 0838, GH 0841, and GH 0842.

Example 9—Biological Activity

Serums and finished ingredients prepared according to various embodiments herein were evaluated for biological activity of interest. The evaluations included in this example are: cytotoxicity; skin sensitization potential; inhibition of trypsin activity; inhibition of elastase activity; inhibition of Kallikrein 5; inhibition of IL-6, IL-8, and/or PGE2; ARE activation; melanin synthesis inhibition; and lipogenesis inhibition. The test methods and results of these evaluations are discussed in more detail below.

Evaluation of Cytotoxicity

Lactate Dehydrogenase (LDH) is a key cytoplasmic enzyme. Presence of LDH outside the cells at levels above normal background leakage is an indicator of cell damage or cell death. Assays quantifying LDH in cell culture medium are commonly employed to assess potential cytotoxicity. Observation of cells under a microscope that identify cell rupture or changes in cell morphology can also contribute to the assessment of cytotoxicity.

Normal human adult epidermal keratinocytes (HEK) and all cell culture supplies in the cytotoxicity evaluation were obtained from Life Technologies Co. (Carlsbad, Calif., USA). The cells were grown and then maintained in keratinocyte basal medium 154 (M154) with added human keratinocyte growth supplements (HKGS) at 37° C. in an atmosphere of 5% $CO_2$ and used between passages 2 to 4. For the experiments, HEK cells were trypsinized, seeded in 96-well plates, and grown to ~80% confluence. HEK were then exposed, or not, to a stress factor, and incubated for 16 hours with or without test articles at various concentrations. After incubation, HEK cell supernatant medium samples were collected, and levels of LDH were evaluated using Cytoscan™ LDH Assay kit (Catalog #786-210, produced by G-Biosciences, St. Louis, Mo., USA). Untreated, unstressed HEK cells were lysed using kit-supplied lysis buffer as a positive control, with lysate used as assay positive control and a measure of maximum LDH release. Lower induced LDH release, when confirmed by microscopy, indicates lower cytotoxicity.

Evaluation of Skin Sensitization Potential

It is possible for a material to not be cytotoxic, and yet be unsafe due to provoking an allergic reaction upon skin contact. Typically, initial exposure to an allergen sensitizes the immune system, and following exposures cause an allergic response. Recent progress in understanding the mechanisms of skin sensitization identified interleukin-18 (IL-18) production in normal human epidermal keratinocytes (HEK) as a useful biomarker for skin contact sensitization (Corsini, et al., "Use of IL-18 Production In a Human Keratinocyte Cell Line to Discriminate Contact Sensitizers from Irritants and Low Molecular Weight Respiratory Allergens." Toxicol In Vitro. 2009 August; 23(5):789-96; Teunis, et al., "Transfer of a Two-tiered Keratinocyte Assay: IL-18 Production by NCTC2544 to Determine the Skin Sensitizing Capacity and Epidermal Equivalent Assay to Determine Sensitizer Potency." Toxicol In Vitro. 2013 April; 27(3): 1135-50). IL-18 is considered a suitable in vitro alternative to animal skin sensitization testing methods such as the Local Lymph Node Assay. Thus, IL-18 production in HEK was evaluated to determine sensitization potential.

Normal human adult epidermal keratinocytes (HEK) were cultured as described above for the cytoxicity evaluation. After incubation with test articles or controls for 16 hours, the HEK cells were lysed with 100 µl/well of 0.5% Triton X-100 in pH 7.4 Phosphate Buffered Saline (PBS). The cell lysates were collected, and IL-18 was quantified using Human IL-18 ELISA Kit (Catalog #7620, produced by MBL International Co., Woburn, Mass., USA). A known skin sensitizer, para-phenylenediamine (pPD) (positive control), significantly induced IL-18 compared to vehicle control in HEK cultures. Fold changes of IL-18 levels between test articles and respective vehicle controls were calculated and compared to pPD. Lower induction of IL-18 indicates lower sensitization potential.

Inhibition of Trypsin Activity

Collagen fibers provide mechanical strength and support for the skin. A ubiquitous protease, trypsin, is associated with damage and inflammation. Trypsin breaks down collagen, potentially leading to decreased mechanical strength of the skin, as well as wrinkles and darkening after stress or injury (Burns T, Breathnach S, Cox N, Griffiths C. Rook's Textbook of Dermatology. Eighth Edition. Wiley-Blackwell, 2010. Vol. 1 Sections 8.21 to 8.27. Vol. 2 Section 29.7).

Trypsin inhibition was determined via an EnzChek kit utilizing casein substrate with intra-molecularly quenched fluorescent label moieties (Catalog # E6638, produced by Life Technologies). Testing was conducted according to manufacturer instructions. Digestion buffer concentrate was diluted in deionized water. Substrate and bovine trypsin (Sigma catalog number T9201) were dissolved and diluted in the digestion buffer. Test articles were dissolved and diluted in digestion buffer. Calibration curve was constructed with amounts of trypsin ranging from 1000 nanograms to about 1.4 nanograms in reaction volume. Soybean trypsin inhibitor, type I-S (Sigma) was used as a positive control.

Amount of trypsin in wells with test articles and controls was fixed at 1000 nanograms. $IC_{50}$ was calculated as concentration of test article in the reaction volume (e.g. microtiter plate well) necessary to reduce the trypsin activity to 50%. Lower $IC_{50}$ values indicate higher potency and a degree of efficacy.

Inhibition of Elastase Activity

Elastin is a protein essential to elastic fiber network contained in connective tissues which depend on elasticity for their function, such as skin. Excessive elastase activity, commonly related to inflammation, degrades elastin and decreases strength and resilience of the skin. During inflammatory processes, elastase can be found in areas beyond those where it is produced or secreted. Human neutrophil elastase inhibition by test articles was determined in kinetic colorimetric assay described by Elastin Products Company, Inc. (Elastin Products Company. Assay with N-MeO-Suc-Ala-Ala-Pro-Val-pNA (EPC No. FH237) as substrate. Elastin Products Company, Inc. Research Biochemicals Catalogue. 2004. p. 84) and modified for its use with 96-well microtiter plates (Corning 3641) from Corning, Inc. (and Synergy 2 microplate reader from BioTek Instruments, Inc. The N-Methoxysuccinyl-Ala-Ala-Pro-Val-pNA substrate (EPC, Catalog No: FH237), and elastase (EPC SE563) were from Elastin Products Company (Owensville, Mich., USA). Working solution of elastase was prepared with 0.15 M pH 7.5 Tris-HCl buffer containing 50 mM NaCl. Working solution of substrate was prepared in 0.15 M pH 5.0 acetate buffer containing 100 mM NaCl, with an aliquot of 2% by volume of final buffer of 1-methyl-2-pyrrolidone used for initial dissolution of the substrate. Deionized water was used to dissolve buffer components. Reaction volume in each well was 224 µl; concentration of elastase was 0.87 units/ml, and substrate, 363 µM.

Enzymatic activity in cleaving the substrate was indicated by a development of yellow color measured as an increase in absorbance at 410 nm wavelength. The mean of maximum rate of absorbance increase in negative control wells was considered as 100% of enzyme activity. $IC_{50}$ was calculated as concentration of test article in the well which reduced the elastase activity to 50%. Lower $IC_{50}$ values indicate higher potency and a degree of efficacy.

Inhibition of Kallikrein 5

Kallikrein 5 (KLK5), also known as stratum corneum tryptic enzyme, is a trypsin-like serine protease. Recent in vitro and in vivo evidence implicates increased levels of KLK5 in augmented inflammatory response such as rosacea (Two A M, Del Rosso J Q, Kallikrein 5-mediated inflammation in rosacea: clinically relevant correlations with acute and chronic manifestations in rosacea and how individual treatments may provide therapeutic benefit. J Clin Aesthet Dermatol. 2014 January; 7(1): 20-5) and in induction of atopic dermatitis-like lesions (Briot A. et al., Kallikrein 5 induces atopic dermatitis-like lesions through PAR2-mediated thymic stromal lymphopoietin expression in Netherton syndrome. J Exp Med. 2009 May 11; 206(5):1135-47). Normal human adult epidermal keratinocytes (HEK) were cultured as described above for the cytoxicity evaluation. After incubation with test articles or controls for 16 hours, HEK cell culture supernatants were collected. KLK5 was quantified using a human KLK5 immunoassay Quantikine ELISA kit (Catalog # DKK500, produced by R&D Systems, Minneapolis, Minn.). The changes of KLK5 concentrations between test articles and vehicle controls were calculated and compared. $IC_{50}$ (concentration of test article necessary to reduce KLK5 levels to 50% compared to samples from untreated cells) values were calculated by sigmoidal curve fitting with SigmaPlot 10.0 (Systat Software). Lower $IC_{50}$ values indicate higher potency and a degree of efficacy.

Inhibition of IL-6 and/or IL-8 Induced by SDS

Normal human adult epidermal keratinocytes (HEK) were cultured as described above for the cytoxicity evaluation. The cells were then incubated with test articles and/or controls for 16 hours. Presence of sodium dodecyl sulfate (SDS) in cell cultivation medium at specific concentrations was used for induction of chemokines and cytokines. IL-8 was induced by 6 µg/mL SDS, IL-6 by 12.5 µg/mL SDS. After incubation, HEK cell supernatants were collected. Quantikine® ELISA kits (R&D Systems Inc, Minneapolis, Minn.) were used to quantify these interleukins in the supernatants. IL-8 was quantified by Human CXCL/IL-8 Immunoassay kit (Catalog # D8000C), and IL-6 was quantified by Human IL-6 Immunoassay kit (Catalog # D6050). $IC_{50}$ (concentration of test article necessary to reduce interleukin levels to 50%, with samples from untreated cells considered as 0% and samples treated solely with respective inducing quantity of SDS as 100%) values were calculated by sigmoidal curve fitting with SigmaPlot 10.0 (Systat Software). Lower $IC_{50}$ values indicate higher potency and a degree of efficacy.

Inhibition of IL-6 and/or IL-8 and/or PGE2 Induced by Full-Spectrum Sunlight from Artificial Source Normal human adult epidermal keratinocytes (HEK) were cultured as described above for the cytoxicity evaluation. The cells were washed once, and M154 was replaced with PBS. Both the washing and the replacement were done with PBS to remove light-absorbing components of M154. The 96-well plate containing HEK was then covered with UV-transparent 1 mm quartz sheet, placed on white underlay atop controlled Peltier-cooled surface maintaining room temperature, and irradiated with a dose of 20 J/cm$^2$ of artificially produced full spectrum sunlight at dose rate of about 1100 W/m$^2$, as measured via pyranometer through same quartz cover. PBS was then removed and replaced with M154, and cells were incubated with test articles and/or controls for 16 hours. Identical manipulations, with exception of presence of sunlight, were carried out with HEK serving as unstressed controls. Irradiation equipment was obtained from Solar Light Company, Glenside, Pa. and included Solar Simulator LS1000-6R-002 in Airmass 1.5 configuration using plain mirror; XPS1000 precision current source, and PMA2144 Pyranometer. After incubation, HEK cell supernatants were collected. Quantikine® ELISA kits (R&D Systems Inc, Minneapolis, Minn.) were used to quantify interleukins in the supernatants. IL-8 was quantified by Human CXCL/IL-8 Immunoassay kit (Catalog # D8000C), IL-6 was quantified by Human IL-6 Immunoassay kit (Catalog # D6050); and PGE2 was quantified using Parameter™ Prostaglandin E$_2$ Assay (Catalog # KGE004B). IC$_{50}$ (concentration of test article necessary to reduce interleukin or prostaglandin levels to 50%, with samples from non-irradiated cells considered as 0% and from irradiated cells considered as 100%) values were calculated by sigmoidal curve fitting with SigmaPlot 10.0 (Systat Software). Lower IC$_{50}$ values indicate higher potency and a degree of efficacy.

Table 7 summarizes the results of evaluating inhibition of IL8 and PGE2 activity induced by full-spectrum sunlight from an artificial source and cytotoxicity (LDH/microscopy).

TABLE 7

| Material | IL8/full spectrum sun induction | PGE2/full spectrum sun induction | Cytotoxicity (LDH/microscopy) |
|---|---|---|---|
| Whole Fruit Extract, Lot 0841 | Some inhibition at low concentrations (~25% inhibition at 0.01%) | Inhibits at low concentrations, IC$_{50}$ 0.01% | Cytotoxic at 0.1% and above |
| Fruit Peel Extract, Lot 0837 | Inhibition at low concentrations (estimated IC$_{50}$ 0.012%, max inhibition 66% at 0.05%) | Inhibits at low concentrations, IC$_{50}$ 0.04% | No cytotoxicity at 0.1% |
| Fruit Peel Serum Fraction, Lot 1082 | No significant inhibition | IC$_{50}$ between 0.003-0.03%. Maximum inhibition 70% at 0.001% | No cytotoxicity at 0.1% |
| Whole Fruit Serum Fraction, Lot 0785 | No significant inhibition | Maximum inhibition 40% at 0.01% | No cytotoxicity at 0.1% |
| Fruit Flesh + Fruit Seed Serum Fraction, Lot 1083 | No significant inhibition | Non-significant inhibition at 0.01-0.02% | No cytotoxicity at 0.1% |

Table 8 summarizes the results of evaluating inhibition of IL8 induced by SDS; KLK5 inhibition; IL18 inhibition; trypsin inhibition; elastase inhibition; and cytotoxicity.

TABLE 8

| Material | IL8 inhibition (SDS) | KLK5 | IL18 | Cytotoxicity (LDH/microscopy) | Trypsin Inhibition | Elastase Inhibition |
|---|---|---|---|---|---|---|
| Achachariu (*Garcinia humilis*) Fruit Peel Serum Fraction, Lot 0822 | Not tested | IC$_{50}$ 0.18% | Maximum 1.46 fold (benchmark sensitizer 7.8 fold) | No cytotoxicity at 0.1% | IC$_{50}$ 0.37% | IC$_{50}$ 0.26% |
| Achachariu (*Garcinia humilis*) Whole Fruit Serum Fraction, Lot 0786 | About 65% inhibition at 0.1% | IC$_{50}$ 0.2% | Maximum 1.8 fold (benchmark sensitizer 7.8 fold) | No cytotoxicity at 0.1% | IC$_{50}$ 0.32% | IC$_{50}$ 0.28% |

In summary, biological activity results suggest that preparations of *achachairu*: (i) are not skin sensitizers; (ii) are not cytotoxic at selected concentrations that could be relevant to their concentrations in finished product formulation; and (iii) potential usefulness for mitigating signs of skin aging caused by inflammation and related process (e.g., those triggered by stresses to the skin, including environmental stress such as full-spectrum sun exposure). More specifically, the test results suggested the following: (i) against PGE2, *achachairu* whole fruit extract is slightly more effective than fruit peel extract; (ii) against PGE2, *achachairu* fruit peel serum fraction is more effective than whole fruit serum fraction, which is tentatively better than fruit flesh+fruit seed serum fraction; and (iii) *achachairu* whole fruit serum fraction is effective for inhibiting SDS-induced IL-8 activity, but not against sun-induced IL8, which is surprising. Also surprising was: (i) the potent inhibition demonstrated by fruit peel extract against sun-induced IL8 and fruit peel serum fraction against sun-induced PGE2; (ii) the lack of any notable activity by fruit flesh+fruit seed serum fraction; (iii) fruit peel serum fraction and whole fruit serum fraction are more cytotoxic than fruit flesh+fruit seed serum fraction; and (iv) whole fruit extract is more cytotoxic than fruit peel extract.

Anti-Oxidant Response Element Activation

The ARE is the so-called "master switch" believed to control the antioxidant defense system of most cells. When the ARE is activated in response to oxidative stress, the corresponding genes signal the cell to begin producing reduction/oxidation regulators and/or reactive oxygen species ("ROS") quenching proteins and enzymes. ROS are highly reactive molecules formed naturally within cells as a natural byproduct of the normal metabolism of oxygen and play a role in cell signaling and homeostasis. However, when a cell is exposed to a stressor such as heat or UV radiation, ROS levels can increase, and in some instances dramatically. As the damage caused by ROS accumulates over time, it causes more and more oxidative stress at the cellular level that ultimately may lead to tissue damage and/or organ dysfunction. Thus, without being limited by theory, it is believed that if *achachairu* can demonstrate the ability to activate the ARE, then applying an effective amount of *achachairu* to keratinous tissue may help fight cellular damage associated with oxidative stress.

ARE activation was quantitated using the ARE-32 reporter cell line available from CXR-Biosciences as described below. ARE-32 is a stable MCF7 cell line containing pGL8x-ARE (8 copies of the rat GST ARE linked to the luciferase gene) and pCDNA3.1, which contains the neomycin selectable marker. Selection was performed in the presence of G418 and resistant clones were isolated. Clones were screened for induction of luciferase in response to tBHQ.

The ARE-32 cells are maintained routinely in Dulbecco's Modified Eagle Medium (phenol red free) ("DMEM") containing: 10% fetal bovine serum ("FBS"), 50 units/ml penicillin & 50 µg/ml streptomycin, 0.8 mg/ml G418. Cells are subcultured every 3-4 days. If needed, cells can be frozen in medium that contains 90% FBS and 10% DMSO.

ARE Method

In a 96 well-plate, $1\times10^4$ cells/well are seeded in 100 µl DMEM containing 50 units/ml penicillin, 50 µg/ml streptomycin, 0.8 mg/ml G418 and 10% FBS. Next, the cells are incubated at 37° C. in a 5% $CO_2$ incubator for 24 hrs, and then the medium is replaced with 100 µl fresh media. The test samples are treated with *achachairu* serum fractions at the concentration listed in Table 11 (1 ul per well), the positive control is 25 uM TBHQ. (10 mM tBHQ of stock solution freshly prepared in DMSO). 100 ul of media is added after treatment for a final assay volume of 200 uL. The cells are incubated at 37° C. in $CO_2$ incubator for another 24 hrs. The test samples are then assayed for luciferase activity with Steady-glo™ brand assay system according to the manufacturer's instruction.

The results of the test are summarized in Table 9. At concentrations of 0.167% to 1.5%, both the whole fruit and peel serum fractions appear to provide more ARE activation than than the control. The whole fruit also demonstrated a directional increase at 0.056% versus the control.

TABLE 9

ARE Activation

| v/v % achachariu | Whole fruit[1] % increase vs control | p-value vs. control | Peel[2] % increase vs control | p-value vs. control |
|---|---|---|---|---|
| 1.5 | 929 | 0.000087 | 1133 | 0.000046 |
| 0.5 | 489 | 0.0023 | 614 | 0.00086 |
| 0.167 | 197 | 0.0076 | 209 | 0.0043 |
| 0.056 | 134 | .0.091 | 113 | 0.67 |
| 0.0185 | 103 | 0.96 | 92 | 0.79 |
| 0.006173 | 112 | 0.83 | 99 | 0.99 |
| 0.002058 | 93 | 0.89 | 92 | 0.94 |
| 0.000686 | 120 | 0.78 | 93 | 0.94 |

[1]Recentia ® GH from AkzoNobel
[2]Recentia ® GH-P from AkzoNobel

Melanin Synthesis Inhibition—B16 Assay

Overproduction of melanin is generally associated with a variety of skin pigmentation conditions (e.g., age spots, vitiligo, solar lentigines, and melasma). Thus, without being limited by theory, it is believed that if *achachairu* can demonstrate the ability to inhibit melanin production, then applying an effective amount of *achachairu* to skin may help improve the appearance of skin pigmentation conditions.

A commercially available B16-F1 mouse melanoma cell line from American Tissue Culture Collection, Virginia, USA was employed in a conventional melanin synthesis inhibition assay. The cell culture medium used in the assay is 500 mL of Dulbecco's Modified Eagle's Medium ("DMEM"), 50 mL Fetal Bovine Serum ("FBS"), and 5 mL of penicillin-streptomycin liquid. B16-F1 cells that are cultured in this medium and grown to greater than 90% confluency will synthesize melanin. While not intending to be bound by theory, it is hypothesized that melanin synthesis is stimulated by the culture medium and/or stress induced by growth to a high confluency. The DMEM and FBS can be obtained from American Tissue Culture Collection and the penicillin-streptomycin liquid can be obtained from Invitrogen, Inc., California, USA. Equipment used in the assay include a $CO_2$ incubator (e.g., a Forma Series Model 3110 by Therma Scientific, Massachusetts, USA or equivalent); a Hemocytometer (e.g., Bright Line model by Hauser Scientific, Pennsylvania, USA or equivalent); and a UV-Visible Spectrum Plate Reader (e.g., SpectraMax250 from Molecular Devices, California, USA or equivalent).

Day 0: To begin the assay, the cell culture medium is heated to 37° C. and 29 mL of the medium is placed into a T-150 flask. Approximately $1\times10^6$ of B16-F1 passage 1 mouse cells are added to the T-150 flask and incubated for 3 days at 37° C., 5% $CO_2$, 90% relative humidity, until ~80% confluency.

Day 3: The cells from the T-150 flask are trypsinized, and the number of cells is determined using the Hemocytometer. Initiate a 96 well plate with 2,500 cells per well in 100 µL of cell culture medium. Incubate the plate at 37° C., 5% $CO_2$, 90% relative humidity for 2 days until at least 20% to 40% confluent.

Day 5: Remove the cell culture medium from the plate and replace with fresh culture medium (100 uL per well). Add 1 uL of test compound diluted in a water solvent. Multiple dilution ratios may be tested in order to generate a dose response curve, wherein preferably three wells are treated with each dilution ratio. Positive and negative controls may include wells having the cell culture medium, B16-F1 cells, and the solvent (negative control), and wells comprising the cell culture medium, B16-F1 cells and and a known melanin inhibitor (e.g., deoxyarbutin or kojic acid).

Day 7: Cells should have greater than ~90% confluency. If not, this data point is not used. Add 100 uL of a 0.75% sodium hydroxide solution to each well. Read the 96-well plate using the UV-Vis Plate Reader at 410 nm to optically measure the amount of melanin produced between wells that are treated with the fava bean extract and control wells that are not. Wells in which melanin is produced appear brownish in color. Wells in which little melanin is produced appear clear to light purple in color. Percentage of melanin synthesis inhibition is calculated by the following equation:

$$\frac{100 - [OD410 \text{ Test Compound} - OD410 \text{ Control \#2}] \times 100}{(OD410 \text{ Control \#1} - OD410 \text{ Control \#2})}$$

Where OD410 is the Optical Density at 410 nm as measured by the UV-Vis Spectrum Plate Reader.

When Control #3 is used, the formula for percentage melanin synthesis inhibition is:

$$\frac{100 - [OD410 \text{ Test Compound} - OD410 \text{ Control \#3}] \times 100}{(OD410 \text{ Control \#1} - OD410 \text{ Control \#2})}$$

The concentration of test agent needed to provide the IC 50 is recorded.

The results of the test are summarized in Table 10, which shows that *achachairu* inhibits melanin synthesis, and thus is expected to provide a skin lightening benefit.

TABLE 10

Melanin Synthesis Inhibition
B16 (IC 50)

| Composition | Concentration Needed for IC 50 (v/v %) |
|---|---|
| Achachariu[1] (whole fruit) | 0.19 |
| Achachariu[2] (peel only) | 0.19 |

[1]Recentia ® GH from AkzoNobel
[2]Recentia ® GH-P from AkzoNobel

Lipogenesis Inhibition

This example demonstrates the ability of *achachairu* to inhibit lipogenesis in human pre-adipocytes. Lipogeneis involves the synthesis of commonly known lipids such as fatty acids and triglycerides, and is one of primary ways mammals store energy. However, lipogenesis also involves the synthesis of lipids such as sebum. Sebum is a lipid produced by sebocytes, which are a type of skin cell found primarily in the sebaceous glands of mammalian skin. Sebum is produced by the body to lubricate and waterproof the skin and hair of mammals. However, overproduction of sebum can result in oily appearing skin and/or skin that appears to have poor texture. Thus, without being limited by theory, it is believed that if *achachairu* can demonstrate the ability to inhibit lipogenesis, then applying an effective amount of *achachairu* to keratinous tissue may help regulate conditions associated with sebum overproduction.

Method

Human pre-adipocytes were selected for use in this example. Because of the known difficulty associated with culturing and testing sebocytes, pre-adipocytes are commonly used as a surrogate for sebocytes to determine the potential of a test agent to inhibit sebum production.

Human subcutaneous pre-adipocytes purchased from Zen-Bio, Inc (Cat. # SP-F-SL) were cultured in PM-1 media (available from Zen-Bio, Inc as Cat# PM-1 (plus 5 ng/ml EGF)) to 80-90% confluency. The cells were transferred to 96-well clear bottom white plates to provide approximately 40,625 cells/cm$^2$ in the well (~12,500 cells) and 150 µl of PM-1 media per well, and then cultured for 24-48 hours in a 5% $CO_2$ incubator at 37° C. The PM-1 media was then replaced with differentiation medium (Zen-Bio, Inc. Cat# DM-1), and the cells were incubated for another 6 days. After incubating in the differentiation medium, 90 µl of the differentiation medium was carefully replaced with 140 µl of human subcutaneous adipocyte medium ((Zen-Bio, Inc. Cat# AM-1). Care was taken not to touch or disturb the cells at the bottom of the well. 2 µl of *achachairu* (Recentia® GH-P for AkzoNoble) or control composition (100 µM Genistein (Cat# G6649) from Sigma) was added to each well daily for 9 days (total incubation of 15 days). On Day 15, 5 µL of AdipoRed reagent (Lonza; Cat. Number: PT-7009) was slowly added directly to cells in the treatment medium, and the plate was gently mixed after each row addition. The plate was incubated for 15 minutes at room temperature. Lipogenesis was quantitated using an EnVision® brand Fluorescent spectrophotometer Plate Reader according to the AdipoRed protocol. The plates were scanned from the bottom using the 451 mirror and (excitation 485 nm; emission 535) filter. Each well was scanned in a Z pattern (7 reads across from left to right, 7 reads diagonally from right to left and 7 reads across from left to right for a total of 21 end points).

Percent inhibition was calculated as:

$$\frac{\text{Average Control } RFU - \text{Sample } RFU}{\text{Average Control } RFU} \times 100$$

The cells were assayed and normalized to the control by using a FluoReporter® Blue Fluorometric brand dsDNA Quantitation Kit. Immediately after the screen the AdipoRed containing cell media was gently aspirated, cells were rinsed with 100 ul 1×PBS taking care not to dislodge them from the bottom and 100 µl distilled water was added/well. The plates were frozen at −80° C. to lyse the cells and assayed according to the kit instructions at a later date.

The results of the test are summarized in Table 11, which shows that *achachairu* inhibits lipogenesis, and thus is expected to help regulate conditions associated with the overproduction of sebum.

TABLE 11

| Lipogenesis Inhibition | |
| --- | --- |
| Compostion | IC 50 w/v % |
| Recentia ® GH-P (achachariu peel) | 0.4% |
| Recentia ® GH (achachariu whole fruit) | 0.5% |

Inhibiting the Cell's Inflammation Response to a Stressor—NF-kappa-beta ("NF-kB") assay.

NF-kB (i.e., nuclear factor kappa-light-chain-enhancer of activated B cells) is a protein complex that belongs to the category of "rapid-acting" primary transcription factors (i.e., transcription factors that are present in cells in an inactive state and do not require new protein synthesis in order to become activated), which allows NF-kB to be a first responder to harmful cellular stimuli such as ROS and other stressors. NP-kB is found in almost all animal cell types and is known to be involved in the cellular inflammation pathway. Cellular inflammation is associated with a variety of skin conditions, and thus inhibiting NF-kB activation vis-á-vis cellular inflammation with an effective amount of *achachairu* may help treat these types of skin conditions.

Method

CellSensor™ NF-κB-bla HEK 293T cells (Invitrogen, Cat. # K1165) were plated in assay medium (DMEM with high glucose (Gibco, Cat. #11965) plus 10% dialyzed FBS). The cells were cultured and seeded at 10,000/well in 96-well plates (black-sided Poly-D-Lysine coated plates, BD #356692), and then incubated at 37° C. and 95% RH for the 72 hours prior to testing. Recombinant human TNFα (available from R&D systems) was used to stimulate NF-kB activation in the cells. Fisetin (3, 7, 3', 4'-tetrahydroxyflavone) was used to inhibit stimulation of the cells by TNFα. A ToxBLAzer™ DualScreen brand screening kit (Invitrogen, Cat. #K1138) was used as the fluorescent substrate according to the manufacturer's instructions.

The following controls were run on each plate in the assay:

High control (Stimulated)=cells+TNFα+1% DMSO

Blank (Unstimulated)=cells+1% DMSO

Standard (Positive control inhibitor)=cells+TNFα+Fisetin+1% DMSO

Negative Control (no cells)=assay medium $$\frac{\text{High Control} - \text{Sample}}{\text{High Control} - \text{Blank}} \times 100$$

NF-κB % inhibition is calculated as:

The results of this test are summarized in Table 12 below. As illustrated in Table 12, the *achachairu* whole fruit serum fractions and *achachairu* peel serum fractions provided an IC 50 for NF-kB inhibition of 2%. Thus, applying an effective amount of *achachairu* to a target portion of keratinous tissue may help regulate conditions related to cellular inflammation.

TABLE 12

| Compostion | IC 50 (v/v %) | Cytotoxicity |
| --- | --- | --- |
| Recentia ® GH-P (Achachariu Peel only) | 2% | None observed |
| Recentia ® GH (Achachariu whole fruit) | 2% | None observed |

Inhibiting the Cell's Inflammation Response to a Stressor-Prostaglandin E2 ("PGE2") assay.

PGE2 is a hormone-like substance that is known to participate in modulation of inflammation. Cellular inflammation is associated with a variety of skin conditions, and thus inhibiting PGE2 activation vis-à-vis cellular inflammation may help treat these types of skin conditions.

Method

Tert keratinocytes ("tKC") were plated at 40,000 cells/well into 24-well plates in 1 ml/well volume. EpiLife Medium (Life Technologies cat # MEPICFPRF500) supplemented with keratinocyte growth supplement (Life technologies cat #S-001-5) was used as the assay media. The cells were grown to confluence/near confluence, and then subjected to 15 mJ/cm² UVB-stress. The test compositions (*achachairu* and vehicle control) (diluted 1:1000) were added, and the plates were incubated for 18-24 hours. The supernatant was removed from each well, and the cells were rinsed with 2 ml/well medium (without supplements). A Cell Titer-Glo assay (measures ATP activity) was conducted on the cells for normalization. The supernatant was tested in a PGE2 assay (Prostaglandin E2 Assay kit from Cisbio Bioassays cat#62P2APEB) according to the manufacturer's instructions. The PGE2 results were normalized to ATP activity.

The results of the PGE2 assay are summarized in Table 13. The *achachairu* whole fruit serum fraction and *achachairu* peel serum fractions both demonstrated the ability to inhibit release of PGE2 from keratinocytes exposed to 15 mJ/cm2 UVB radiation, which illustrates anti-inflammatory activity of *achachairu*. Thus, a personal care composition comprising *achachairu* may be useful for regulating a skin condition related to cellular inflammation.

TABLE 13

| Test | PGE2 Release (% of vehicle control) | StDev |
| --- | --- | --- |
| Recentia ® GH-P Achachariu peel | 28% | 8.20% |
| Recentia ® GH (Achachariu whole fruit) | 52% | 11.40% |
| Vehicle control | 98% | 13.20% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving the appearance and/or feel of skin, comprising:
   a. identifying a target portion of skin in need of treatment or where treatment is desired; and
   b. applying a skin care composition comprising an effective amount of *achachairu* serum fraction to the target portion of skin during a treatment period, wherein the treatment period is sufficient for the *achachairu* serum fraction to provide a skin care benefit, and wherein the *achachairu* serum fraction is obtained from *achachairu* juice that is processed to have a dry matter content of less than 25%, by weight of the serum fraction.

2. The method of claim 1, wherein the *achachairu* serum fraction is obtained from a peel of an *achachairu* fruit.

3. The method of claim 1, wherein the *achachairu* serum fraction is substantially free of at least one of benzophenone and protein.

4. The method of claim 1, wherein the *achachairu* serum fraction is applied to the target portion of skin at least once per day.

5. The method of claim 1, wherein the *achachairu* serum fraction is present in the skin care composition at an amount of from about 0.01% to about 15%.

6. The method of claim 1, wherein the skin care composition further comprises about 20% to about 99.99% of a dermatologically acceptable carrier.

7. The method of claim 1, wherein the skin care composition further comprises at least one additional active selected from the group consisting of vitamins, minerals, peptides, sugar amines, anti-oxidants, preservatives, anti-inflammatory agents, moisturizing agents, skin lightening agents, particles, anti-wrinkle actives, anti-atrophy actives, N-acyl amino acid compounds, and combinations of these.

8. The method of claim 1, wherein the skin care composition comprises a preservative selected from pentylene glycol, tetrasodium EDTA, sodium metabisulfite, potassium sorbate, or sodium benzoate.

9. The method of claim 1, wherein the skin care benefit is selected from the group consisting of an anti-inflammatory benefit, an anti-aging benefit, an anti-oxidant benefit, and a lipogenesis inhibition benefit.

10. The method of claim 3, wherein the *achachairu* serum fraction is substantially free of benzophenone and protein.

* * * * *